United States Patent
Endo

(10) Patent No.: US 9,863,918 B2
(45) Date of Patent: Jan. 9, 2018

(54) ULTRASONIC MEASUREMENT DEVICE, HEAD UNIT, PROBE, AND DIAGNOSTIC DEVICE

(71) Applicant: SEIKO EPSON CORPORATION, Tokyo (JP)

(72) Inventor: Kogo Endo, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 281 days.

(21) Appl. No.: 14/062,151

(22) Filed: Oct. 24, 2013

(65) Prior Publication Data
US 2014/0116139 A1    May 1, 2014

(30) Foreign Application Priority Data
Oct. 25, 2012    (JP) .................... 2012-235420

(51) Int. Cl.
*G01N 29/04*    (2006.01)
*G01N 29/24*    (2006.01)
*B06B 1/06*    (2006.01)
*A61B 8/00*    (2006.01)

(52) U.S. Cl.
CPC ....... *G01N 29/2437* (2013.01); *A61B 8/4483* (2013.01); *A61B 8/4494* (2013.01); *B06B 1/0622* (2013.01); *A61B 8/4411* (2013.01); *A61B 8/4488* (2013.01); *G01N 2291/106* (2013.01)

(58) Field of Classification Search
CPC ...................... G01N 29/2437; G01N 2291/106
USPC .......................................................... 73/584
See application file for complete search history.

(56) References Cited

U.S. PATENT DOCUMENTS

| | | | | |
|---|---|---|---|---|
| 5,893,363 A | * | 4/1999 | Little | A61B 8/00 600/447 |
| 5,920,972 A | * | 7/1999 | Palczewska | B06B 1/064 29/25.35 |
| 7,654,961 B2 | * | 2/2010 | Tezuka | B06B 1/0629 367/140 |

(Continued)

FOREIGN PATENT DOCUMENTS

| | | |
|---|---|---|
| CN | 1507150 A | 6/2004 |
| CN | 1802036 A | 7/2006 |

(Continued)

*Primary Examiner* — Lisa Caputo
*Assistant Examiner* — Tarun Sinha
(74) *Attorney, Agent, or Firm* — Global IP Counselors, LLP

(57) ABSTRACT

An ultrasonic measurement device includes a substrate, an ultrasonic element array, an ultrasonic transducer device, and an integrated circuit device. The ultrasonic element array has a plurality of ultrasonic elements arranged on the substrate. The ultrasonic transducer device is formed on the substrate and having a plurality of signal electrode lines electrically connected to the ultrasonic element array. The integrated circuit device has a plurality of terminals to output a transmission signal to the ultrasonic element array. Each of the signal electrode lines includes an electrode layer in which at least one signal electrode among some of the ultrasonic elements is formed to extend on the substrate. The integrated circuit device is mounted on the substrate, and each of the terminals of the integrated circuit device is connected to a corresponding one of the signal electrode lines.

19 Claims, 18 Drawing Sheets

(56) References Cited

U.S. PATENT DOCUMENTS

| | | | |
|---|---|---|---|
| 2004/0024320 A1* | 2/2004 | Karasawa | B06B 1/0622 |
| | | | 600/459 |
| 2004/0169444 A1 | 9/2004 | Higuchi et al. | |
| 2007/0244392 A1 | 10/2007 | Tezuka | |
| 2008/0064232 A1 | 3/2008 | Reiss et al. | |
| 2009/0250729 A1 | 10/2009 | Lemmerhirt et al. | |
| 2011/0115333 A1* | 5/2011 | Ezaki | B06B 1/0292 |
| | | | 310/300 |
| 2011/0181149 A1* | 7/2011 | Shikata | B06B 1/0629 |
| | | | 310/327 |
| 2011/0201934 A1* | 8/2011 | Robinson | G01S 7/5208 |
| | | | 600/443 |
| 2011/0237952 A1* | 9/2011 | Ooishi | A61B 8/00 |
| | | | 600/459 |
| 2011/0316389 A1* | 12/2011 | Kwon | B06B 1/0622 |
| | | | 310/335 |
| 2012/0123263 A1* | 5/2012 | Osaka | A61B 8/08 |
| | | | 600/438 |
| 2012/0256520 A1* | 10/2012 | Torashima | H01L 41/0815 |
| | | | 310/300 |
| 2013/0175877 A1* | 7/2013 | Abe | H04B 5/0037 |
| | | | 307/104 |

FOREIGN PATENT DOCUMENTS

| | | | | |
|---|---|---|---|---|
| CN | 101145551 A | 3/2008 | | |
| CN | 201286719 Y | 8/2009 | | |
| JP | 2005-341085 A | 12/2005 | | |
| JP | WO 2012102075 A1 * | 8/2012 | | H04B 5/0037 |

* cited by examiner

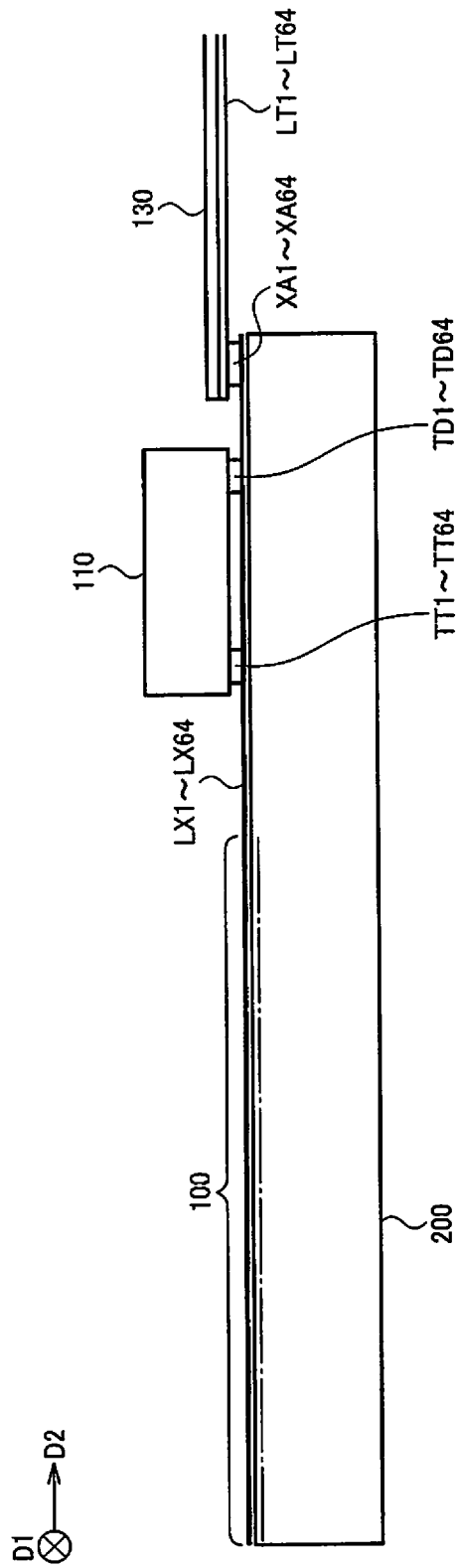

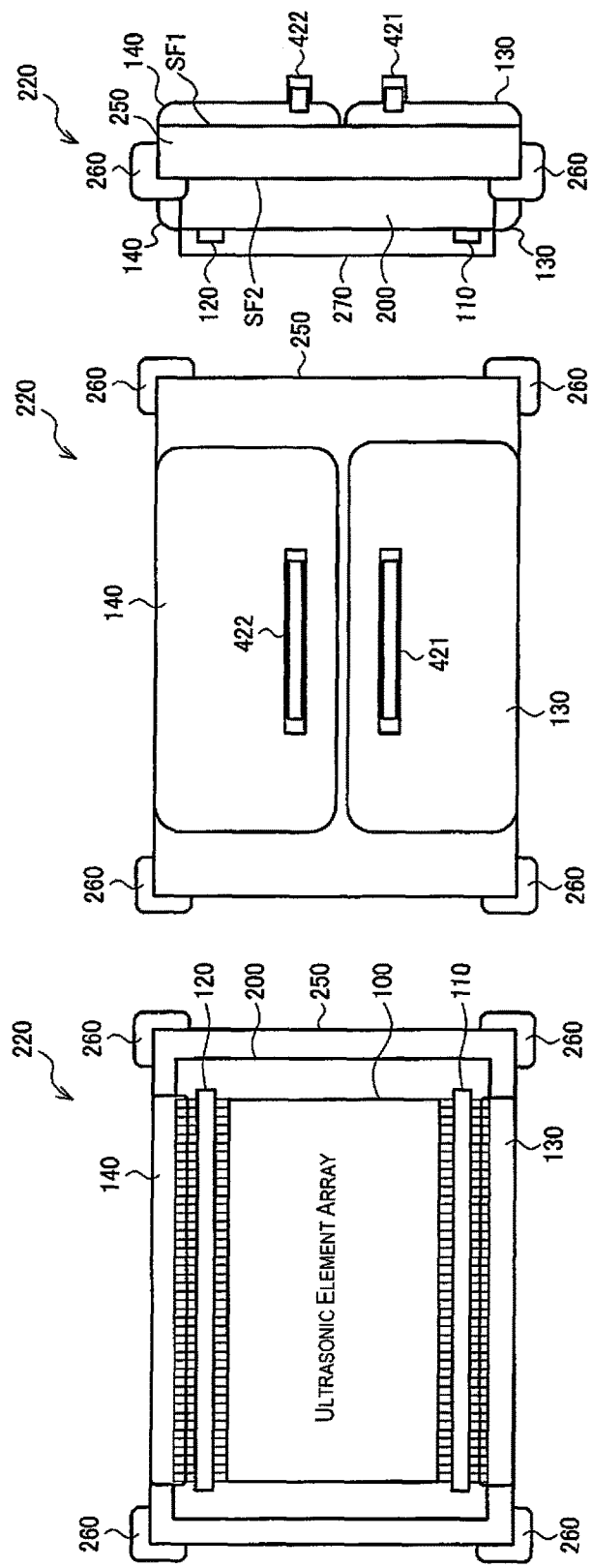

ULTRASONIC MEASUREMENT DEVICE, HEAD UNIT, PROBE, AND DIAGNOSTIC DEVICE

CROSS-REFERENCE TO RELATED APPLICATIONS

This application claims priority to Japanese Patent Application No. 2012-235420 filed on Oct. 25, 2012. The entire disclosure of Japanese Patent Application No. 2012-235420 is hereby incorporated herein by reference.

BACKGROUND

Technical Field

The present invention relates to an ultrasonic measurement device, a head unit, a probe, a diagnostic device, and the like.

Related Art

For example, in Japanese Laid-open Patent Application No. 2005-341085, it discloses an ultrasonic probe in which an insulator layer is provided from a part of a back electrode of a piezoelectric member in bulk to the side surface of the piezoelectric member, and a conductive layer is provided to continue to a front electrode of the piezoelectric member and wrap around the back electrode side, and a wire formed on a flexible substrate is connected to the conductive layer and the back electrode on the back surface side of the piezoelectric member.

SUMMARY

Conventionally, a piezoelectric member in bulk is used as an ultrasonic element to transmit and receive an ultrasonic wave. However, a high voltage at, for example, approximately 100V is required to drive the piezoelectric member in bulk so that it is necessary to use a drive IC that is high-voltage resistance. Generally, a mounting area of the high-voltage resistance IC becomes large and the number of the ICs is increased so that there is a problem to reduce the size of the device in which the ICs are mounted.

According to some aspects of the present invention, an ultrasonic measurement device, a head unit, a probe, a diagnostic device, and the like that enable miniaturization of a device can be provided.

One aspect of the present invention relates to an ultrasonic measurement device including a substrate, an ultrasonic element array, an ultrasonic transducer device, and an integrated circuit device. The ultrasonic element array has a plurality of ultrasonic elements arranged on the substrate. The ultrasonic transducer device is formed on the substrate and having a plurality of signal electrode lines electrically connected to the ultrasonic element array. The integrated circuit device has a plurality of terminals to output a transmission signal to the ultrasonic element array. Each of the signal electrode lines includes an electrode layer in which at least one signal electrode among some of the ultrasonic elements is formed to extend on the substrate. The integrated circuit device is mounted on the substrate, and each of the terminals of the integrated circuit device is connected to a corresponding one of the signal electrode lines.

According to one aspect of the present invention, a signal electrode of the ultrasonic element is formed and extended as a signal electrode wiring on the substrate of the ultrasonic transducer device. The integrated circuit device is mounted on the substrate of the ultrasonic transducer device, and in the mounting condition, each terminal of the plurality of terminals of the integrated circuit device is connected to any of the plurality of signal electrode lines. Because of this, miniaturization of a device becomes possible.

In one aspect of the present invention, the ultrasonic element array is a rectangle, and when the long side direction of the rectangle is defined as the first direction, the integrated circuit device is mounted on the substrate so as to form the long side direction of the integrated circuit device along the first direction, and the plurality of signal electrode lines may be formed on the substrate along the second direction that intersects the first direction.

Accordingly, the integrated circuit can be mounted on the substrate so as to oppose the plurality of terminals of the integrated circuit to the long side of the ultrasonic element array. And, by connecting the plurality of terminals and the plurality of signal electrode lines on the substrate, the integrated circuit device and the ultrasonic element array can be connected in a simple wiring.

In one aspect of the present invention, each ultrasonic element of the plurality of ultrasonic elements has the first electrode, the second electrode, and a transducer section that is provided between the first electrode and the second electrode. The first electrode or the second electrode may be extendedly formed on the substrate as at least one of the signal electrode lines.

Because of this, without providing other wire member, it is possible to connect from the electrode of the transducer member to the signal terminal of the ultrasonic transducer device by the signal electrode wire that was extendedly formed on the substrate.

In one aspect of the present invention, the plurality of terminals of the integrated circuit device is configured by a bump electrode, and the integrated circuit device may be subjected to flip chip mounting to the substrate.

Accordingly, the integrated circuit device is subjected to a flip chip mounting so that the mounting area can be reduced in comparison with the case that it is mounted on a rigid substrate of a probe main body by, for example, a flat package, and the like. Therefore, the ultrasonic measurement device can be minimized.

In one aspect of the present invention, a circuit element of the integrated circuit device is formed on a silicon substrate, and the substrate of the ultrasonic transducer device may be configured by silicon.

Accordingly, by connecting the silicon substrates that have the same coefficient of thermal expansion, it can be realized that the integrated circuit device is mounted on the substrate of the ultrasonic transducer device with high connection reliability in comparison with a connection of different materials that have different coefficient of thermal expansion.

In one aspect of the present invention, a vibration film of the ultrasonic element array is formed on the substrate, and at least one of the signal electrodes may be extendedly formed on the vibration film.

Accordingly, the vibration film that vibrates by the ultrasonic element of the ultrasonic element array is formed, and by extendedly forming the signal electrode of the ultrasonic element on the vibration film, the plurality of signal electrode lines can be formed on the substrate.

In one aspect of the present invention, a second integrated circuit device, which is mounted on the substrate, is further included. The ultrasonic element array is a rectangle, and the integrated circuit device is mounted in the first long side of the rectangle, and the second integrated circuit device may be mounted in the second long side of the rectangle.

Accordingly, a transmission signal can be applied from both ends of a plurality of ultrasonic element rows that configures the ultrasonic element array. Because of this, even when a transmission signal is attenuated by reason of which, for example, the signal electric wires connected to the ultrasonic element rows are high-value resistance, it is possible to form symmetrical ultrasonic beam by applying a transmission signal from the both ends of the ultrasonic element rows.

In one aspect of the present invention, the ultrasonic element array is a rectangle, and the integrated circuit device has a transmission circuit, which outputs the transmission signal, in each of the plurality of terminals. When the long side direction of the rectangle is defined as the first direction, in the state that the integrated circuit device is mounted on the substrate, the plurality of transmission circuits is arranged along the first direction. The ultrasonic element array is a rectangle, and the integrated circuit device has a plurality of transmission circuits, which outputs the transmission signal to the plurality of terminals. When the long side direction of the rectangle is defined as the first direction, in the state that the integrated circuit device is mounted on the substrate, the plurality of transmission circuits may be arranged along the first direction.

Accordingly, by arranging the plurality of transmission circuit along the first direction, it is possible to form an elongated shaped-integrated circuit device. Because of this, it is possible that the integrated circuit device is mounted on the substrate so as to oppose the plurality of transmission circuits to the long side of the ultrasonic element array. Because of this, the plurality of signal electrode lines, which connects between the plurality of transmission circuits and the ultrasonic element array, can be a simple wiring.

In one aspect of the present invention, the integrated circuit device has a transmission and reception selector switch connected to the terminal, and the plurality of transmission and reception selector switches may be arranged along the first direction in the state that the integrated circuit device is mounted on the substrate.

Accordingly, a transmission signal from the transmission circuit is suppressed to input to a reception circuit so that it is possible to protect the reception circuit from the electric breakdown. Also, by arranging the plurality of transmission and reception selector switches along the first direction, the layout arrangement can be efficiently obtained for the elongated integrated circuit device.

In one aspect of the present invention, the integrated circuit device has a multiplexer arranged between the plurality of terminals, which is arrayed and arranged along the first direction, and the plurality of transmission circuits, which is arrayed and arranged along the first direction.

Accordingly, the plurality of transmission circuits, the multiplexer, and the plurality of terminals can be arranged along the flow of signals outputted to the plurality of terminals through the multiplexer from the plurality of transmission circuits.

In one aspect of the present invention, a protective film layer that protects the ultrasonic element array may be formed on the substrate and the integrated circuit device that is mounted on the substrate.

Accordingly, the integrated circuit device that is mounted on the substrate of the ultrasonic transducer device can be protected by the protective film layer that protects the ultrasonic element array.

In one aspect of the present invention, the protective film layer may be combined with an acoustic matching layer.

Accordingly, the integrated circuit device that is mounted on the substrate of the ultrasonic transducer device can be protected by the protective film layer that combines with the acoustic matching layer.

In one aspect of the present invention, the substrate has a plurality of openings arranged in an array pattern. Each ultrasonic element of the plurality of ultrasonic elements has a vibration film, which covers a corresponding one of the openings, and a piezoelectric element section, which is provided on the vibration film. The piezoelectric element section has a lower electrode, which is provided on the vibration film, a piezoelectric film, which is provided to cover at least a part of the lower electrode, and an upper electrode, which is provided to cover at least a part of the piezoelectric film.

Accordingly, each ultrasonic element of the ultrasonic element array can be configured by the ultrasonic element so as to vibrate the vibration film, which covers the opening, by the piezoelectric element. Because of this, it is possible to drive the ultrasonic element by a low-voltage drive signal in comparison with the case of using the piezoelectric element in bulk. The integrated circuit device is manufactured in the low-voltage resistance process so that it is possible to form the integrated circuit device in a compact size.

Another aspect of the present invention relates to a head unit of a probe that includes any of the ultrasonic measurement devices described above and is a detachable head unit with respect to the probe main body of the probe.

Further, another aspect of the present invention relates to a probe that has a probe main body and any of the ultrasonic measurement devices disclosed above, and includes a detachable head unit with respect to the probe main body.

Further, another aspect of the present invention relates to a diagnostic device that includes any of the ultrasonic measurement devices disclosed above and a display section, which displays image data for display.

BRIEF DESCRIPTION OF THE DRAWINGS

Referring now to the attached drawings which form a part of this original disclosure:

FIG. 6 is a basic configuration example of an ultrasonic measurement device of the present embodiment.

FIG. 17A to FIG. 17C are a detailed configuration example of a head unit.

DETAILED DESCRIPTION OF EXEMPLARY EMBODIMENTS

Hereinafter, preferred embodiment of the present invention will be described. The present embodiment described below shall not be construed as unreasonably limiting the subject matter of the present invention described in the claims, and all the elements described in the present embodiment are not necessarily essential to the solving means of the present invention.

1. Ultrasonic Element

As described above, there is a problem that when the ultrasonic element in bulk is used, the high-voltage resistance drive IC is required so that it is difficult to minimize the device. For example, in a portable type ultrasonic measurement device, and the like, there is a need to minimize its probe or device main body. However, when the high-voltage resistance drive IC is mounted, it disturbs the miniaturization.

In Japanese Laid-open Patent Application No. 2005-341085 described above, the electrode of the bulk piezoelectric member, which is the ultrasonic element, is connected to the transmission and reception section through the flexible substrate. In the flexible substrate, a wire that connects between the electrode and the transmission and reception section is only formed so that there is a problem of the increase of the number of components or the costs.

Also, almost entire integrated circuit device (IC) that drives the ultrasonic element is mounted on the main substrate that is a rigid substrate so that it is assumed that the IC is configured by a flat package and the IC occupies large area in the main substrate. In addition, a semiconductor process that tolerates high voltage of approximately 100V to drive the bulk piezoelectric member is required so that the mounting area of the IC becomes larger. Because of this, in the method of Japanese Laid-open Patent Application No. 2005-341085, there is a problem of the difficulty of achieving miniaturization of a device in the case that it applies to, for example, a portable type ultrasonic measurement device, and the like.

Also, if it intends to minimize a device with the use of the IC that the mounting area is large as described above, the area or the number of the drive ICs is reduced by the reduction of the number of drive channels so that there is a problem of the reduction of the number of channels of the ultrasonic element array. When the number of channels is reduced, the convergent of the ultrasonic beam is reduced so that the resolution that is an important characteristic of the ultrasonic diagnostic device is deteriorated.

The ultrasonic measurement device of the present embodiment that can solve these problems will be described below. First, the ultrasonic element applied to the ultrasonic measurement device of the present embodiment will be described.

Figure 1A:
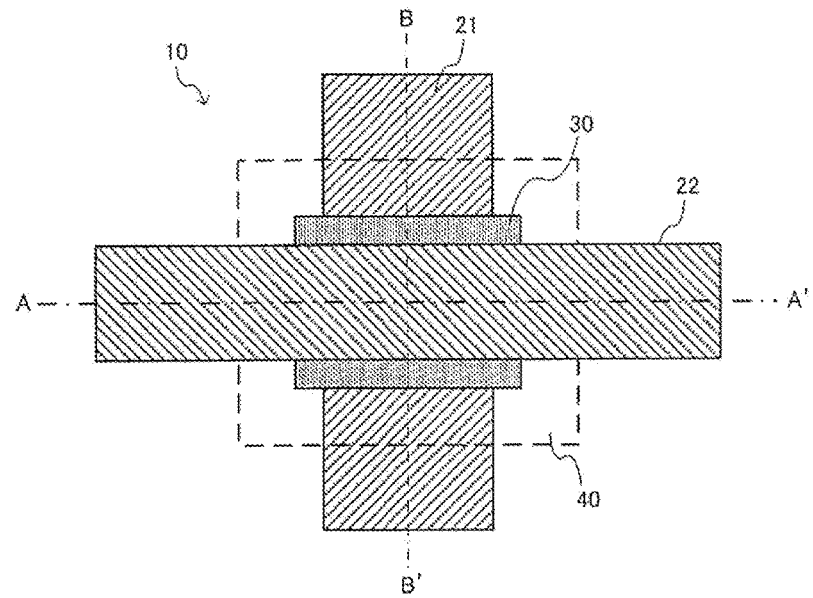
FIG. 1A to FIG. 1C are configuration examples of an ultrasonic element of the present embodiment.
Figure 1B:
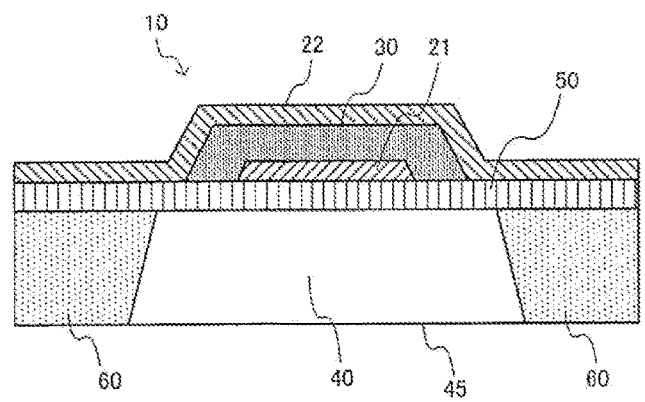
Figure 1C:
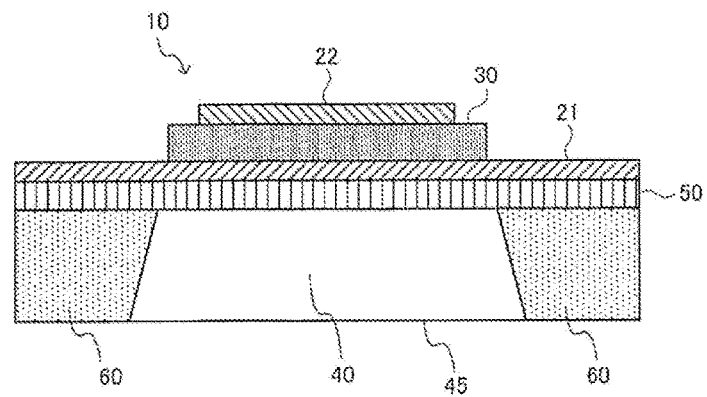

A configuration example of an ultrasonic element 10 applied to the ultrasonic measurement device of the present embodiment is shown in FIG. 1A to FIG. 1C. The ultrasonic element 10 is provided with a vibration film (membrane, support member) 50 and a piezoelectric element section. The piezoelectric element section is provided with a lower electrode (first electrode layer) 21, a piezoelectric layer (piezoelectric film) 30, and an upper electrode (second electrode layer) 22.

FIG. 1A is a plan view, which is viewed in a direction perpendicular to the substrate in an element formation side, of the ultrasonic element 10 formed in the substrate (e.g., silicon substrate) 60. FIG. 1B is a cross-sectional diagram showing a cross-section along A-A' of FIG. 1A. FIG. 1C is a cross-sectional diagram showing a cross-section along B-B' of FIG. 1A.

The first electrode layer 21 is formed by, for example, a metal thin film on an upper layer of the vibration film 50. The first electrode layer 21 is extended to the outside of the element formation area as shown in FIG. 1A, and may be a wire that connects to the adjacent ultrasonic element 10.

For example, the piezoelectric layer 30 is formed by a piezoelectric zirconate titanate (PZT) thin film, and it is provided to cover at least a part of the first electrode layer 21. By the way, the material of the piezoelectric layer 30 is not limited to PZT so that for example, lead titanate ($PbTiO_3$), lead zirconate ($PbZrO_3$), lead lanthanum titanate ($(Pb,La)TiO_3$) may be used.

The second electrode layer 22 is formed by, for example, a metal thin film, and it is provided to cover at least a part of the piezoelectric layer 30. The second electrode layer 22 is extended to the outside of the element formation area as shown in FIG. 1A, and may be a wire that connects to the adjacent ultrasonic element 10.

The vibration film (membrane) 50 is provided to cover the opening 40 by two layers structure, for example, $SiO_2$ thin film and $ZrO_2$ thin film. The vibration film 50 supports the piezoelectric layer 30, and the first electrode layer 21 and the second electrode layer 22, and it vibrates in accordance with the expansion and contraction of the piezoelectric layer 30 so as to generate the ultrasonic wave.

The openings 40 are arranged in an array pattern on a substrate 60. A cavity region of the opening 40 is formed by etching such as reactive ion etching (RIE), and the like from the back surface (the surface where an element is not formed) side of the substrate 60. A resonance frequency of the ultrasonic wave is determined by the size of the opening section 45 of the cavity region, and the ultrasonic wave is radiated to the piezoelectric layer 30 side (forward direction from the back surface on a page in FIG. 1A).

The first electrode of the ultrasonic element 10 is formed by the first electrode layer 21, and the second electrode is formed by the second electrode layer 22. Specifically, a portion that is covered by the piezoelectric layer 30 in the first electrode layer 21 forms the first electrode, and a portion that covers the piezoelectric layer 30 in the second electrode layer 22 forms the second electrode. That is, the piezoelectric layer 30 is provided between the first electrode and the second electrode.

The piezoelectric layer 30 stretches in-plane direction by applying a voltage between the first electrode and the second electrode, that is, the first electrode layer 21 and the second electrode layer 22. The ultrasonic element 10 uses a monomorph (unimorph) structure in which a thin piezoelectric element (piezoelectric layer 30) and a metal plate (vibration film 50) are bonded together, and when the piezoelectric layer 30 stretches in-plane, the dimension of the bonded vibration film 50 is unchanged so as to occur warping. By applying alternating voltage to the piezoelectric layer 30, the vibration film 50 vibrates in a film thickness direction so that the ultrasonic wave is radiated by the vibration of the vibration film 50.

The voltage applied to the piezoelectric layer 30 is, for example, 10V to 30V, and the frequency is, for example, 1 MHz to 10 MHz. That is, it can be driven in the low-voltage in comparison with the case that the piezoelectric element in bulk is used, and it is possible to manufacture the drive IC in the low-voltage resistance semiconductor process. Because of this, it is possible to provide the ultrasonic diagnostic device in a compact size or with multi-channels.

2. Ultrasonic Transducer Device (Element Chip)

Figure 2:
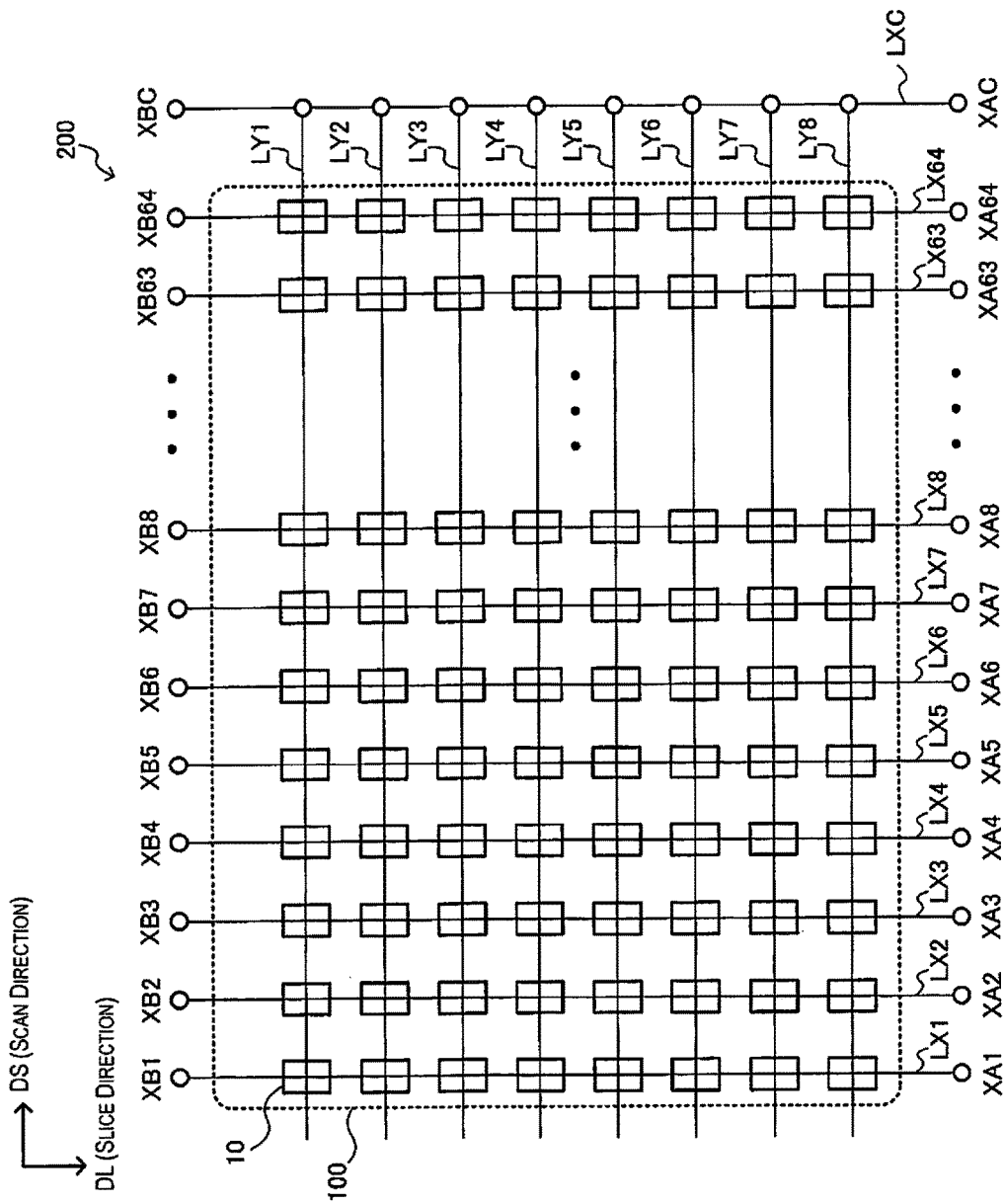
FIG. 2 is a configuration example of an ultrasonic transducer device of the present embodiment.

FIG. 2 shows a configuration example of an ultrasonic transducer device 200 that includes the ultrasonic measurement device of the present embodiment. The ultrasonic transducer device 200 includes the substrate 60 (not shown in FIG. 2), an ultrasonic element array 100 formed on the substrate 60, $1^{st}$ to n-th signal terminals XA1 to XAn (plurality of signal terminals), n+1-th to second signal terminals XB1 to XBn (second plural signal terminals), a first common terminal XAC, and a second common terminal XBC.

The ultrasonic element array 100 includes a plurality of ultrasonic elements 10, which is arranged in the m-rows and n-columns matrix array pattern, the $1^{st}$ to n-th signal electrode lines LX1 to LXn, the $1^{st}$ to m-th common electrode wires LY1 to LYm, and a common electrode wire LXC. For example, the ultrasonic elements 10 can be configured as shown in FIG. 1A to FIG. 1C. By the way, as an example, the case of m=8, n=64 will be described below. However, the present embodiment is not limited to this so that m and n may be other values.

As shown in FIG. 2, the $1^{st}$ row to 8th row of the ultrasonic elements 10 are arranged along a slice direction DL, and the $1^{st}$ column to the 64th column of the ultrasonic elements 10 are arranged along a scan direction DS that intersects with the slice direction DL. Here, the scan direction means a direction that scans the ultrasonic beam in sector scan or linear scan The $1^{st}$ to $64^{th}$ of the signal electrode lines LX1 to LX64 are arranged along the slice direction DL in the ultrasonic element array 100, and a drive voltage is supplied to each of the 1st to $64^{th}$ of the ultrasonic elements 10. One end of the $1^{st}$ to $64^{th}$ of the signal electrode lines LX1 to LX64 is connected to the $1^{st}$ to $64^{th}$ of the signal terminals XA1 to XA64, respectively, and the other end of the $1^{st}$ to $64^{th}$ of the signal electrode lines LX1 to LX64 is connected to the $65^{th}$ to $128^{th}$ of the signal terminals XB1 to XB64, respectively. The signal electrode lines LX1 to LX64 are formed by which the first electrode layer 21 and the second electrode layer 22 of FIG. 1A extends on the substrate 60 to the signal terminals XA1 to XA64. Here, the phrase "extendedly formed on the substrate 60" means that the conductive layer (wire layer) is laminated on the substrate by, for example, a MEMS process, a semiconductor process, and the like, and at least two points (e.g., from the ultrasonic element to the signal terminal) are connected by the conductive layer.

The $1^{st}$ to $8^{th}$ common electrode wires LY1 to LY8 are wired along the scan direction DS, and common voltage is supplied to the plurality of ultrasonic elements of the ultrasonic element array 100. The $1^{st}$ to $8^{th}$ common electrode wires LY1 to LY8 are connected to the common electrode wire LXC that is wired along the slice direction DL. The first common terminal XAC is connected to one end of the common electrode wire LXC, and the second common terminal XBC is connected to the other end of the common electrode wire LXC.

Each wire of the $1^{st}$ to $64^{th}$ signal electrode lines LX1 to LX64 corresponds to one of the first electrode layer 21 and the second electrode layer 22 described in FIG. 1A etc., and each wire of the $1^{st}$ to $8^{th}$ common electrode wires LY1 to LY8 corresponds to the other one of the first electrode layer 21 and the second electrode layer 22.

In FIG. 2, an example in the case that one column of the ultrasonic elements 10 lined in the slice direction DL is connected to one channel (one signal terminal) is described, but the present embodiment is not limited to this so that a plural columns of ultrasonic elements lined in the slice direction DL may be connected to one channel. For example, when 6 columns of the ultrasonic elements are connected to one channel, the ultrasonic element array 100 becomes m rows and 6n columns of the matrix array pattern.

In FIG. 2, an example in the case that the ultrasonic element array 100 arranges m rows and n columns of matrix pattern is described, but the present embodiment is not limited to this so that it is acceptable when the plurality of unit elements (ultrasonic elements) has an arrangement that is an array pattern having two-dimensional regularity. For example, the ultrasonic element array 100 may be zigzag pattern. Here, the arrangement of the matrix pattern means the grid arrangement of m rows and n columns, and it is not only the case that the grid is rectangle, but also includes the case that the grid is changed to parallelogram. The zigzag arrangement means that m rows of the ultrasonic elements and m-1 columns of the ultrasonic elements are alternately lined, and m columns of the ultrasonic elements are arranged in odd row of (2m-1) rows and m-1 columns of the ultrasonic elements are arranged in even row of (2m-1) rows.

3. Basic Configuration of Ultrasonic Measurement Device

FIG. 3 to FIG. 6 show a basic configuration example of the ultrasonic measurement device of the present embodiment. The ultrasonic measurement device is provided with an ultrasonic transducer device 200, a first flexible substrate 130, a second flexible substrate 140, a first integrated circuit device 110 that is mounted on the substrate 60 of the ultrasonic transducer device 200, and a second integrated circuit device 120 that is mounted on the substrate 60 of the ultrasonic transducer device 200. In the following, the first integrated circuit device 110 will be described as an example of the first flexible substrate 130, but the second integrated circuit device 120 and the second flexible substrate 140 may be configured in the same manner. Also, in the following, the ultrasonic transducer device 200 is appropriately called as an element chip.

Figure 3:
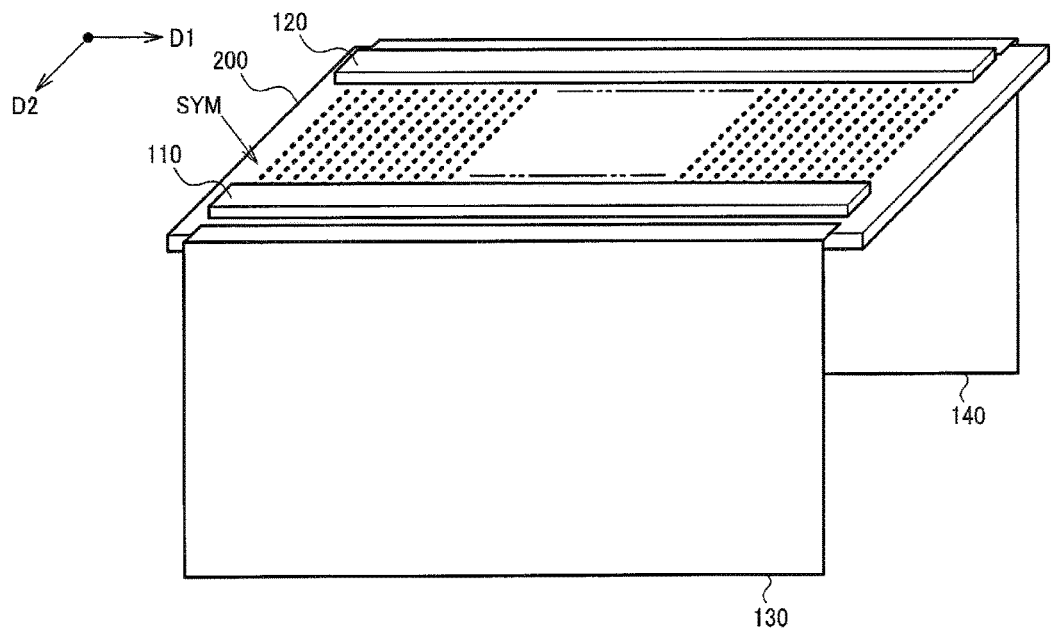
FIG. 3 is a basic configuration example of an ultrasonic measurement device of the present embodiment.
Figure 4:
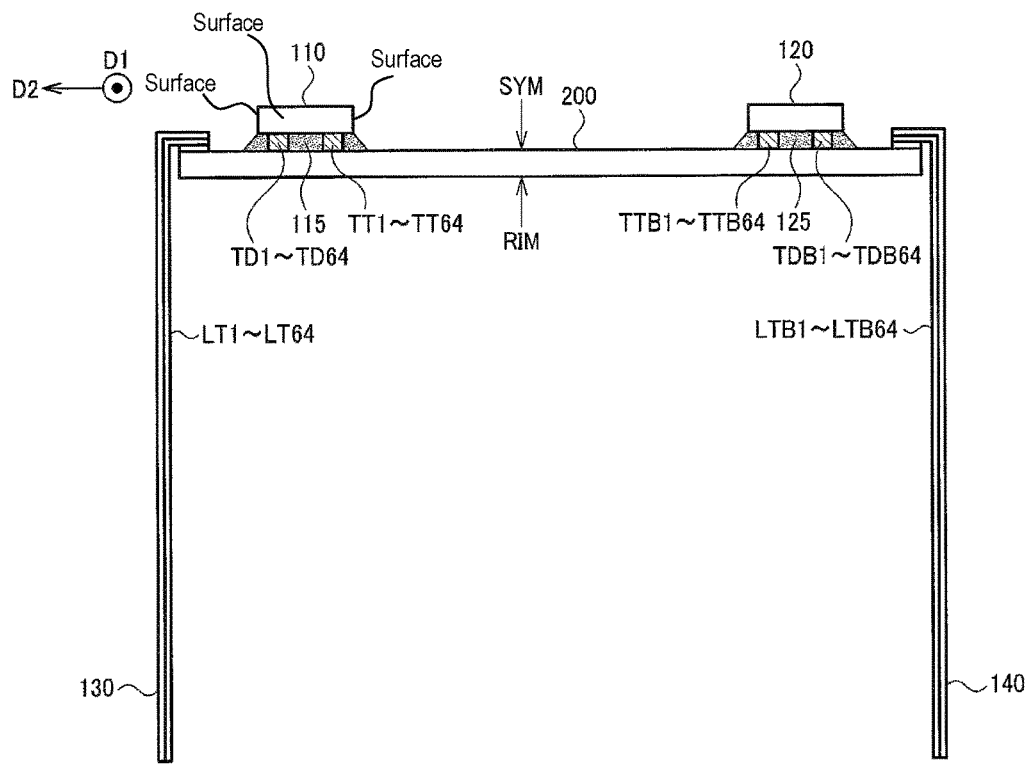
FIG. 4 is a basic configuration example of an ultrasonic measurement device of the present embodiment.

The first direction D1 shown in FIG. 3 and FIG. 4 corresponds to the scan direction DS of FIG. 2, and the second direction D2 intersecting the first direction D1 corresponds to the slide direction DL of FIG. 2. That is, the $1^{st}$ to $64^{th}$ signal electrode lines LX1 to LX64 are formed on the substrate 60 of the element chip 200 along the second direction D2. Also, the 1$^{st}$ to 64$^{th}$ signal electrode lines LX1 to LX64 are formed on the surface SYM on the ultrasonic radiation direction side (that is, the side where the piezoelectric layer 30 is formed) of the element chip 200. The integrated circuit device 110 is mounted on the surface SYM on the ultrasonic radiation direction side of the element chip 200. In the state of mounting, the 1$^{st}$ to 64$^{th}$ transmission terminals TT1 to TT64 of the integrated circuit device 110 are connected to the 1$^{st}$ to 64$^{th}$ signal electrode lines LX1 to LX64 of the element chip 200.

The 1$^{st}$ to 64$^{th}$ signal wires LT1 to LT64 (plurality of signal wires) are formed in the flexible substrate 130. The 1$^{st}$ to 64$^{th}$ signal wires LT1 to LT64 are formed inner side (right side towards the page in FIG. 4) of the flexible substrate 130, and are connected to the 1$^{st}$ to 64$^{th}$ signal terminals XA1 to XA64 of the element chip 200. The other ends of the 1$^{st}$ to 64$^{th}$ signal wires LT1 to LT64 are extended to the other end of the flexible substrate 130, and are connected to connecter terminals, and the like to connect to, for example, a latter part of circuit substrate. The signal wires LT1 to LT64 are connected to the signal terminals XA1 to XA64 so that the surface that the signal wires LT1 to LT64 of the flexible substrate 130 are formed is opposed to the surface SYM of the ultrasonic radiation direction side of the element chip 200. And, the flexible substrate 130 is bent to the opposite direction side (back surface RIM side of the element chip 200) of the ultrasonic radiation direction.

Figure 10:
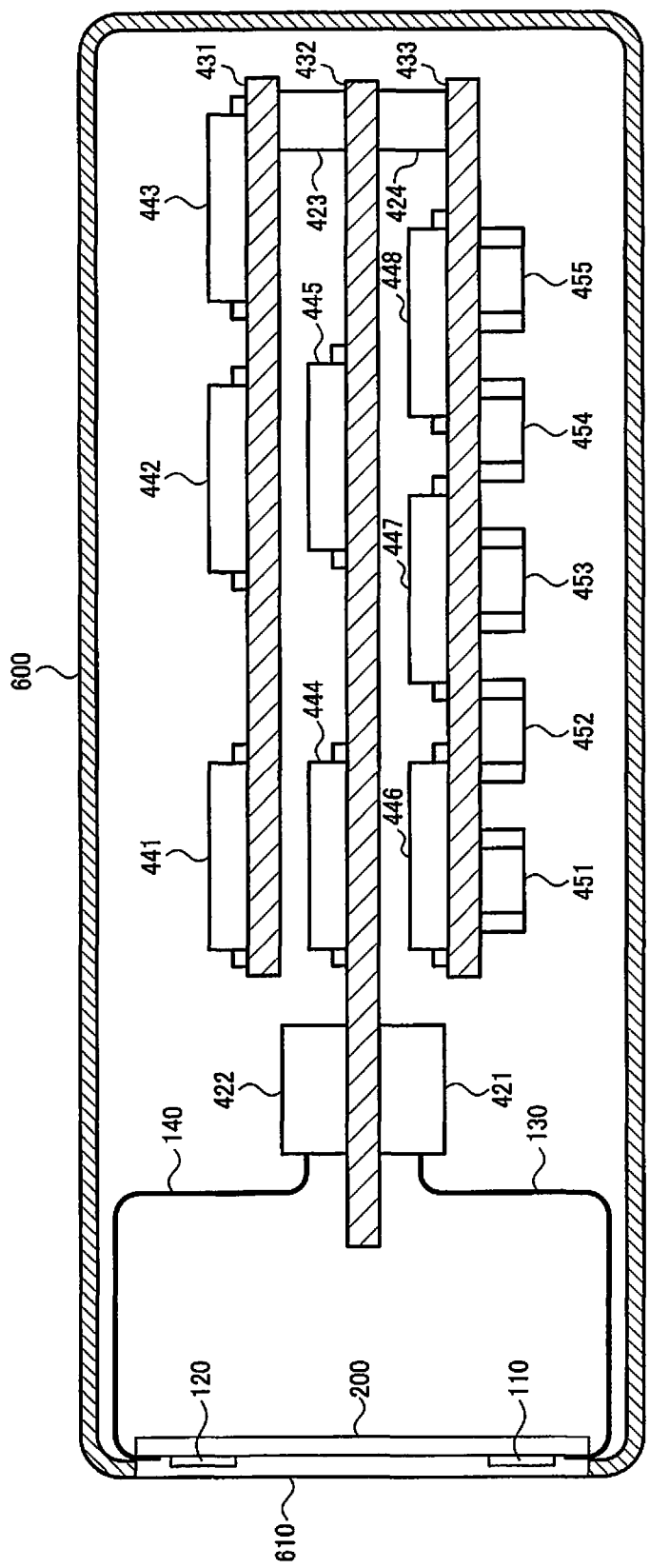
FIG. 10 is a configuration example of an ultrasonic probe.

Here, the phrase "bent to the opposite direction side of the ultrasonic radiation direction" means that the end portion (end portion on the side where the element chip 200 is not connected) of the flexible substrate 130 is bent so as to extend to the back surface RIM side of the element chip 200, at least. For example, as shown in FIG. 10, and the like, the flexible substrate 130 is bent so that the end portion of the flexible substrate 130 is wrapped around the back surface RIM of the element chip 200. In the example of FIG. 10, the end portion of the flexible substrate 130 that was wrapped around the back surface RIM is connected to a connector 421.

Figure 5:
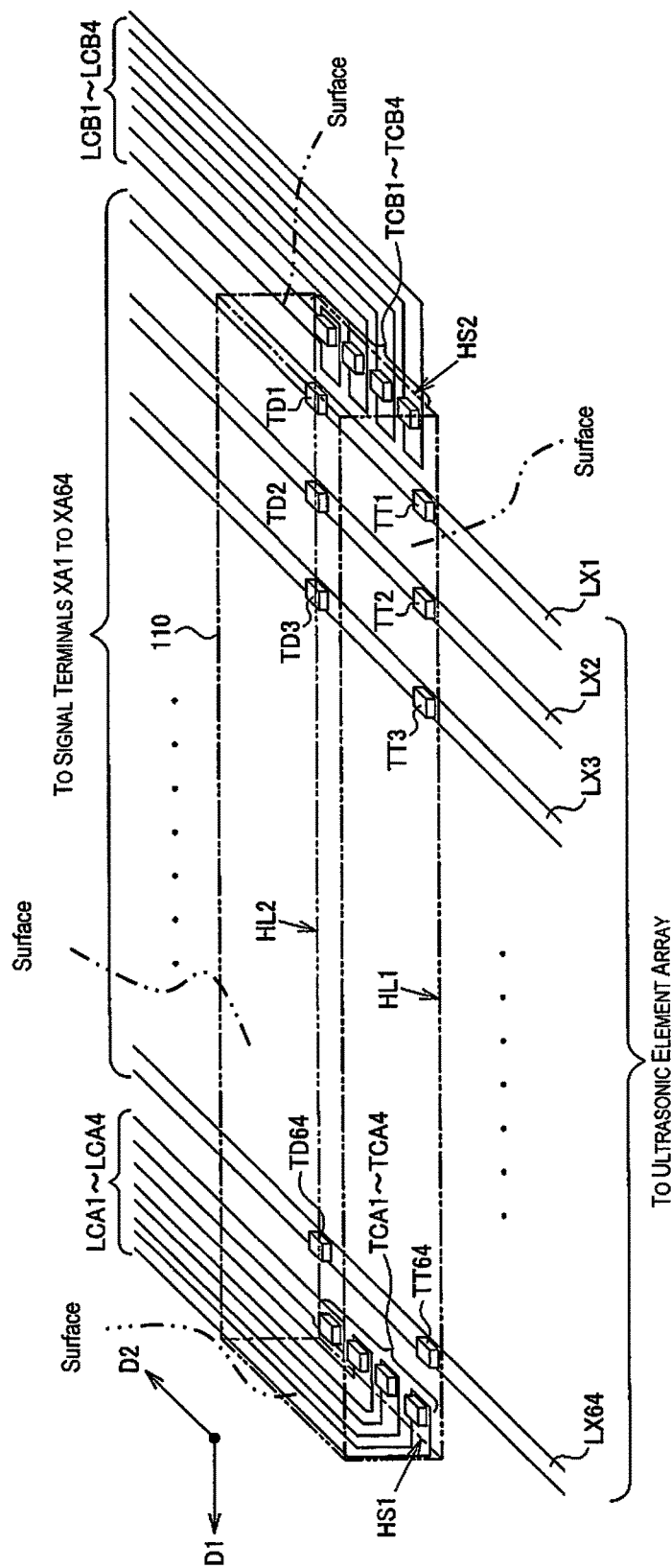
FIG. 5 is a basic configuration example of an ultrasonic measurement device of the present embodiment.

As shown in FIG. 5 and FIG. 6, in the integrated circuit device 110, the 1$^{st}$ to 64$^{th}$ transmission terminals TT1 to TT64 (plurality of transmission terminals) are arranged along the first long side HL1 of the integrated circuit device 110, and the 1$^{st}$ to 64$^{th}$ dummy terminals TD1 to TD64 (plurality of dummy terminals) are arranged along the second long side HL2 of the integrated circuit device 110. Also, in the integrated circuit device 110, control terminals TCA1 to TCA 4, TCB1 to TCB4 can be arranged along the first short side HS1 and the second short side HS2 of the integrated circuit device 110. These terminals are a bump terminal, and, for example, it is formed by applying metal plating to a pad terminal of the integrated circuit device 110. Alternatively, a resin layer that becomes as an insulating layer, a metal wire, and a bump terminal that is connected to the metal wire may be formed on the element formation surface of the integrated circuit device 110.

Here, the "dummy terminal" is a terminal that does not output or input a signal such as, for example, a transmission signal, a reception signal, a control signal, and the like, and for example, it forms only a bump terminal and it is a terminal that a circuit is not connected to the bump terminal. By the way, the dummy terminal may include a test terminal that performs signal input and output in a test step of the manufacturing process. Further, an electrostatic protection circuit may be connected to the dummy terminal.

The integrated circuit device 110 is mounted on the substrate 60 of the element chip 200 so as to form the long sides HL1, HL2 along the direction D1, and form the long side HL1 on the transmission terminals TT1 to TT64 side toward the ultrasonic element array 100 side. At the time of mounting, the 1$^{st}$ to 64$^{th}$ transmission terminals TT1 to TT64 and the 1$^{st}$ to 64$^{th}$ dummy terminals TD1 to TD64 of the integrated circuit device 110 are connected to the 1$^{st}$ to 64$^{th}$ signal electrode lines LX1 to LX64 of the element chip 200. In a plan view that the substrate 60 is viewed from the mounting side of the integrated circuit device 110, the 1$^{st}$ to 64$^{th}$ signal electrode lines LX1 to LX64 are formed through under the integrated circuit device 110.

As shown in FIG. 5, at the time of mounting, the control terminals TCA1 to TCA4, TCB1 to TCB4 of the integrated circuit device 110 are connected to the control signal wires LCA1 to LCA4, LCB1 to LCB4. The control signal wires LCA1 to LCA4, LCB1 to LCB4 are a conductive wire formed on the substrate 60, and for example, it is formed in the wire layer which is the same as the first electrode layer 21 and the second electrode layer 22 described in FIG. 1A, etc. In the control signal wires LCA1 to LCA4, LCB1 to LCB4, for example, a transmission pulse signal or a transmission and reception control signal is supplied from a transmission and reception control circuit 560 of FIG. 8, and the integrated circuit device 110 generates a transmission signal based on the transmission pulse signal or the transmission and reception control signal. Also, it is not shown, but a common output terminal may be provided in the integrated circuit device 110. The common output terminal supplies a common voltage to the ultrasonic element array 100 through a wire on the substrate 60.

Next, the operation of the above described ultrasonic measurement device will be described. A transmission signal (hereinafter referred to as "drive signal") from the integrated circuit device 110 is inputted to the ultrasonic element array 100 through the 1$^{st}$ to 64$^{th}$ transmission terminals TT1 to TT64 and the 1$^{st}$ to 64$^{th}$ signal electrode lines LX1 to LX64. The ultrasonic element array 100 irradiates an ultrasonic wave by the transmission signal, and the ultrasonic wave is reflected from an observation object, and the reflected wave is received by the ultrasonic element array 100. At the time of receiving the ultrasonic wave, the reception signal from the ultrasonic element array 100 is outputted to the 1$^{st}$ to 64$^{th}$ signal wires LT1 to LT64 of the flexible substrate 130 through the 1$^{st}$ to 64$^{th}$ signal electrode lines LX1 to LX64 and the 1$^{st}$ to 64$^{th}$ signal terminals XA1 to XA64. And, the reception signal is outputted to a latter part of reception circuit (for example, an analog front end circuit 550 in FIG. 8). The detailed circuit configuration of the integrated circuit device 110 will be described later.

In the mounting of the integrated circuit device 110 as described above, as shown in FIG. 4, it is realized by the flip chip mounting (bare chip mounting) that uses the anisotropic conductive film (ACF) 115. Specifically, the anisotropic conductive film 115 is a resin film including conductive particles such as metal fine particles, and the like. When the anisotropic conductive film 115 is interposed and the integrated circuit device 110 adheres to the substrate 60, and the anisotropic conductive film 115 is hardened by heat, the anisotropic conductive film 115 is cured and shrunken so that the integrated circuit device 110 and the substrate 60 are pulled each other by the curing shrinkage. A projection terminal (bump) of the integrated circuit device 110 crushes the conductive particles so that it makes conduction for the wires of the substrate, and the integrated circuit device 110 is supported by that the projection terminal is against the force of the curing shrinkage. In a portion of the film that is not oppressed by the terminal, a space between the conductive particles maintains in the insulating state so that the terminal does not occur short circuit.

In this way, it is subjected to a flip chip mounting to the substrate 60 by using the anisotropic conductive film 115 so that the mounting area can be reduced in comparison with the case that the integrated circuit device of the flat package is mounted to the latter portion of the print substrate (rigid substrate). Also, the integrated circuit device 110 can be minimized since it is possible to drive the element chip 200 of the present embodiment in approximately 10 to 30V. Therefore, the miniaturization by the flip chip mounting, which is difficult to be realized in the bulk piezoelectric element due to the requirement of the high voltage resistance of the integrated circuit device, can be easily realized. Also, the substrate 60 is configured by the silicon substrate in the same manner as the integrated circuit device 110. That is, since they are bonded in the same coefficient of thermal expansion, the mounting that the reliability of bonding is high can be realized in comparison with the bonding of the different materials that have different coefficient of thermal expansion.

By the way, the flip chip mounting may be, for example, a face-down mounting so that the element formation surface faces on the substrate 60 side and is mounted. Alternatively, it may be a face-up mounting so that the back surface of the element formation surface faces on the substrate 60 side and is mounted.

Figure 7A:
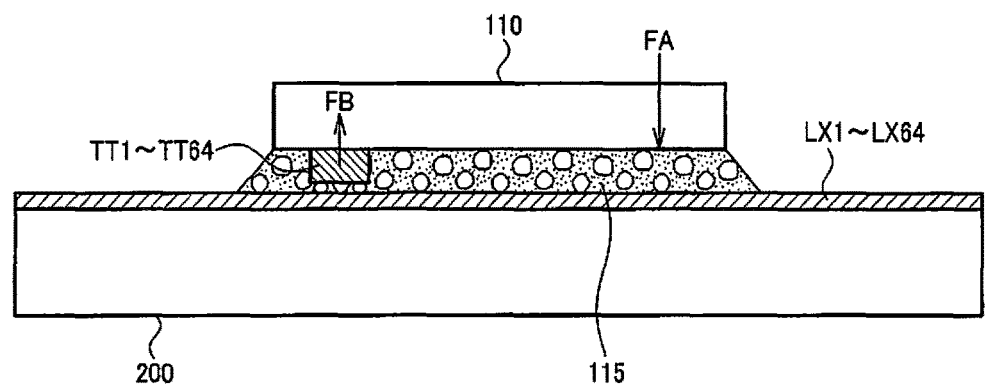
FIG. 7A and FIG. 7B are an explanatory diagram for a dummy terminal.

FIG. 7A is a cross-sectional diagram of a portion where the integrated circuit device 110 is mounted on the ultrasonic transducer device 200 when the dummy terminals TD1 to TD64 are not provided. As shown in FIG. 7A, when the $1^{st}$ to $64^{th}$ transmission terminals TT1 to TT64 are existed on one side (one side of the long side) of the integrated circuit device 110, the force of the curing shrunken of the anisotropic conductive film 115 becomes uneven on the side where the terminals are existed and on the side where the terminals are not existed. As a result of the unevenness, the force FA of the integrated circuit device 110 and the substrate 60 pulling against each other occurs on the side where the terminals are not existed. On the other hand, on the side where the $1^{st}$ to $64^{th}$ transmission terminals TT1 to TT64 are formed, the force FB that lifts the $1^{st}$ to $64^{th}$ transmission terminals TT1 to TT64 is generated by the force FA so that the $1^{st}$ to $64^{th}$ transmission terminals TT1 to TT64 may be lifted from the $1^{st}$ to $64^{th}$ signal electrode lines LX1 to LX64.

Figure 7B:
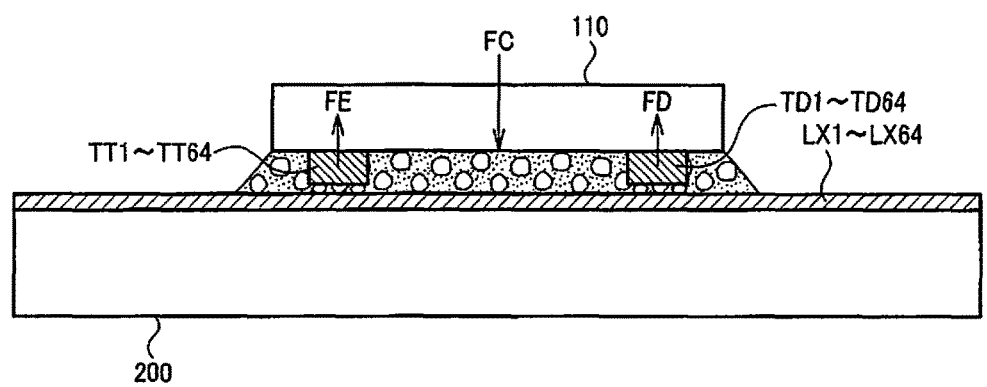

In this point, in the present embodiment, the $1^{st}$ to $64^{th}$ transmission terminals TT1 to TT64 are provided on the first long side HL1 of the integrated circuit device 110, and the $1^{st}$ to $64^{th}$ dummy terminals TD1 to TD64 are provided on the second long side HL2. Because of this, as shown in FIG. 7B, the force FE against the $1^{st}$ to $64^{th}$ transmission terminals TT1 to TT64 and the force FD against the $1^{st}$ to $64^{th}$ dummy terminals TD1 to TD64 become balanced with respect to the force FC of the curing shrunken of the anisotropic conductive film 115 so that the forces are balanced and the conduction between the $1^{st}$ to $64^{th}$ transmission terminals TT1 to TT64 and the $1^{st}$ to $64^{th}$ signal electrode lines LX1 to LX64 can be maintained.

By the way, in the present embodiment, it is not limited to the anisotropic conductive film (ACF) 115 so that for example, the integrated circuit device 110 may be mounted on the substrate 60 by using the Anisotropic Conductive Paste (ACP), the Non-Conductive Film (NCF), the Non-Conductive Paste (NCP), and the like.

The second integrated circuit device 120 and the second flexible substrate 140 are configured in the same manner as described above. That is, as shown in FIG. 4, etc., the second integrated circuit device 120 is mounted on the surface SYM on the ultrasonic radiation direction side of the element chip 200 by the flip-chip mounting using the anisotropic conductive film 125. In the mounting state, the $1^{st}$ to $64^{th}$ transmission terminals TTB1 to TTB64 (second plurality of transmission terminals) of the second integrated circuit device 120 are connected to the $1^{st}$ to $64^{th}$ signal electrode lines LX1 to LX64 of the element chip 200. In the second flexible substrate 140, the $1^{st}$ to $64^{th}$ signal wires LTB1 to LTB64 (second plurality of signal wires) are formed. The signal wires LTB1 to LTB64 are connected to the $65^{th}$ to $128^{th}$ signal terminals XB1 to XB64 (second plurality of signal terminals) of the element chip 200.

Accordingly, two integrated circuit devices 110 and 120 are provided and the ultrasonic element array 100 is driven from the both sides of the element rows so that a symmetrical shape of the ultrasonic beam can be realized. That is, when the signal electrode lines LX1 to LX64 have a high resistance, the shape of the ultrasonic beam in the slice direction DL may be asymmetric by the attenuation of the drive signal, but the shape of the ultrasonic beam in the slice direction DL can be symmetric by performing both-side drive as described in the present embodiment.

In the present embodiment, it is not limited to the both-side drive as described above so that it may be one-side drive. That is, the flexible substrate 130 and the integrated circuit device 110 are only provided, and a drive signal may be supplied from only one side of the signal terminals XA1 to XA64 of the element chip 200.

4. Detailed Configuration of Ultrasonic Measurement Device

Figure 8:
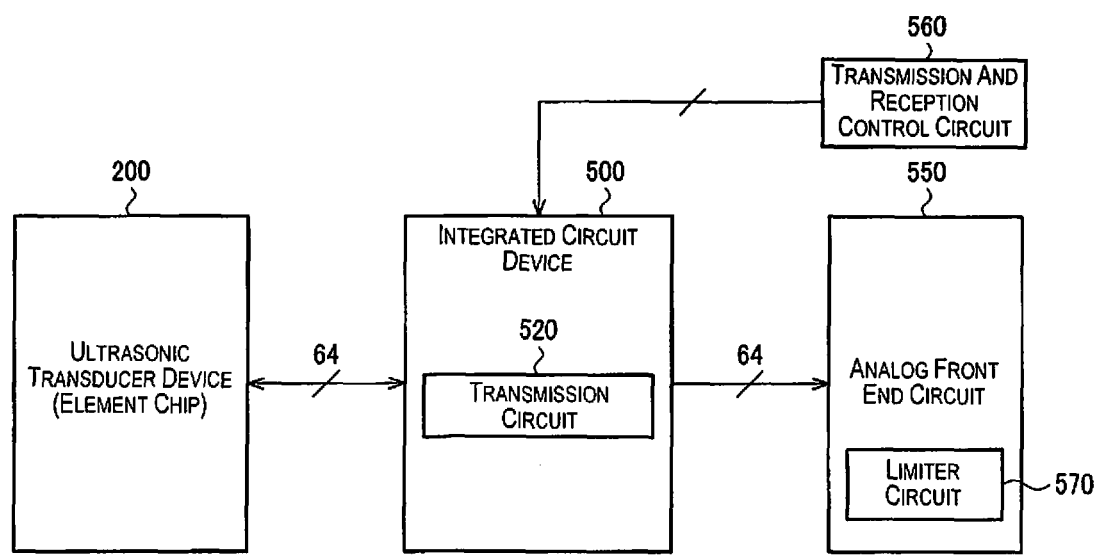
FIG. 8 is a circuit block diagram of a configuration example of an ultrasonic measurement device of the present embodiment.

FIG. 8 shows a circuit block diagram of a configuration example of an ultrasonic measurement device. The ultrasonic measurement device is provided with the element chip 200, an integrated circuit device 500, an analog front end circuit 550, and a transmission and reception control circuit 560. By the way, an example that the integrated circuit device 500 corresponds to the first integrated circuit device 110 will be described below, but the integrated circuit device 500 may correspond to the second integrated circuit device 120, or it may include both of the first integrated circuit device 110 and the second integrated circuit device 120.

The transmission and reception control circuit 560 performs the transmission control or the reception control of the ultrasonic wave to the integrated circuit device 500. The transmission and reception control circuit 560 supplies the control signals to the integrated circuit device 500 through the control signal wires LCA1 to LCA4, LCB1 to LCB4 and the control terminals TCA1 to tCA4, TCB1 to TCB4 shown in FIG. 5.

A reception signal is inputted to the analog front end circuit 550 from the element chip 200 through the flexible substrate 130, and the analog front end circuit 550 performs a reception process such as, for example, an amplification process, an A/D converting process, and the like. Also, the analog front end circuit 550 includes a limiter circuit 570 limiting a high voltage transmission signal that the integrated circuit device 500 outputs. The integrated circuit device 500 that drives the element chip 200 is operated by approximately 10V to 30V, and the analog front end circuit 550 is operated by few volts so that when the transmission signal is directly inputted to the analog front end circuit 550, the analog front end circuit 550 may be destroyed (electrostatic discharge damage). Therefore, the limiter circuit 570 is provided so that the transmission signal is not inputted to the analog front end circuit 550. By the way, it may not be the limiter circuit 570, and a switch element that turns off during the transmission period of the ultrasonic wave may be provided.

Figure 9:
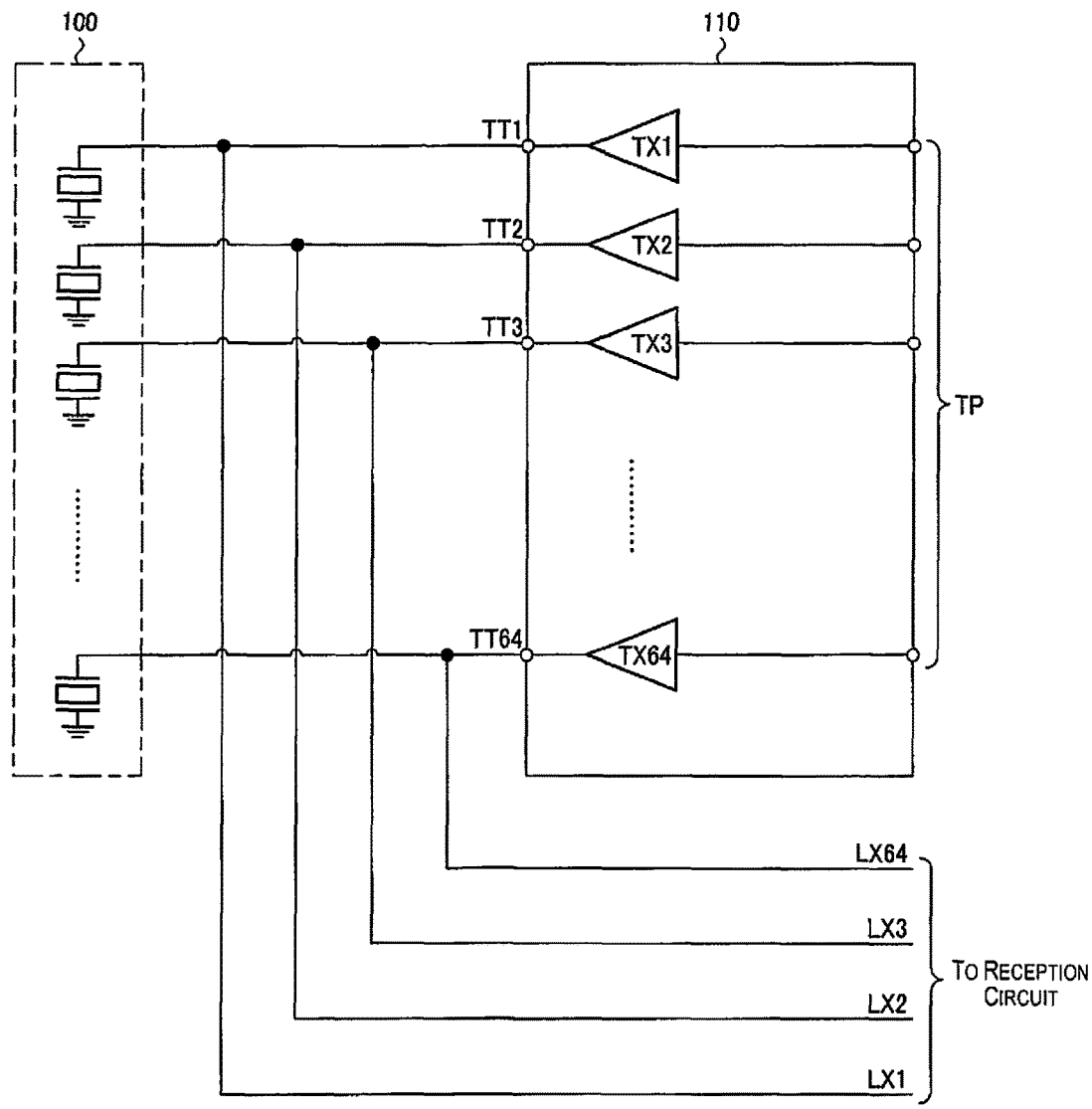
FIG. 9 is a detailed configuration example of an integrated circuit device of the present embodiment.

The integrated circuit device 500 is provided with a transmission circuit 520 that amplifies a transmission pulse signal from the transmission and reception control circuit 560. FIG. 9 shows the detailed configuration example of the integrated circuit device 110 corresponding to the integrated circuit device 500. The integrated circuit device 110 includes the $1^{st}$ to $64^{th}$ transmission circuit TX1 to TX64. The $1^{st}$ to $64^{th}$ transmission circuits TX1 TX64 correspond to the transmission circuit 520 of FIG. 8. By the way, the integrated circuit device 120 can be configured in the same manner.

During the transmission period of the ultrasonic wave, the transmission and reception control circuit 560 supplies a transmission pulse signal to the $1^{st}$ to $64^{th}$ transmission circuit TX1 to TX64 through the terminal group TP. Here, the terminal group TP includes the control terminals TCA1 to TCA4, TCB1 to TCB4 of FIG. 5. The $1^{st}$ to $64^{th}$ transmission circuits TX1 to TX64 amplify the supplied transmission pulse signal, and the transmission pulse signal is outputted to the ultrasonic element array 100 through the $1^{st}$ to $64^{th}$ transmission terminals TT1 to TT64.

During the reception period of the ultrasonic wave, the ultrasonic element array 100 receives a reflection wave of the ultrasonic wave from an observation object, and the reception signal is inputted to the analog front end circuit 550 through the $1^{st}$ to $64^{th}$ signal electrode lines LX1 to LX64. The reception signal passes the limiter circuit 570 without any limitation since it is very small (voltage magnitude is small) in comparison with the transmission signal, and it is inputted to the reception circuit of the analog front end circuit 550, and the like.

In the case of performing a phase scan, the transmission and reception control circuit 560 can include a phase control circuit (delay circuit), which is not shown, that performs a phase control of a transmission signal and a reception signal. Specifically, the phase control circuit delays a transmission pulse signal from the $1^{st}$ to $64^{th}$ transmission circuits TX1 to TX64, and performs a phase scan of the ultrasonic beam. Here, the phase scan means to control the phase difference between the transmission signals, and to scan in a radiation direction (beam direction) of the ultrasonic wave. And, during the reception period, the analog front end circuit 550 delays the reception signal according to the phase difference at the time of transmission, and arranges phases between the reception signals so as to perform the reception process.

Also, in the case of performing a linear scan, the transmission circuit that outputs a transmission signal is selected based on an instruction from the transmission and reception control circuit 560. Specifically, in a case that a linear scan that drives 8 channels at once is exemplified, the $1^{st}$ to $8^{th}$ transmission circuits TX1 to TX8 output a transmission pulse signal during the first transmission period, and the $2^{nd}$ to $9^{th}$ transmission circuits TX2 to TX9 output a transmission signal during the second transmission period. Because of this, the ultrasonic element array 10 is driven while sequentially shifting the ultrasonic element rows, which is driven. At the time of reception, first, the analog front end circuit 550 receives a reception signal from the $1^{st}$ to $8^{th}$ signal electrode lines LX1 to LX8 during the first reception period, and the analog front end circuit 550 receives a reception signal from the $2^{nd}$ to $9^{th}$ signal electrode lines LX2 to LX9 during the second reception period. Because of this, an ultrasonic wave is received while sequentially shifting the ultrasonic element rows.

By the way, the ultrasonic measurement device of the present embodiment is not limited to the above configuration so that, for example, it may be a configuration that the linear scan is not be performed and the phase scan is only performed, or it may be a configuration that a phase scan is not performed, and the linear scan is only performed.

5. Ultrasonic Probe

FIG. 10 shows a configuration example of an ultrasonic probe including an ultrasonic measurement device of the present embodiment. The ultrasonic probe is provided with a case 600, an acoustic member 610, an element chip 200 (ultrasonic transducer device), integrated circuit devices 110, 120, flexible substrates 130, 140, connectors 421 to 424, rigid substrates 431 to 433, integrated circuit devices 441 to 448, and circuit elements 451 to 455.

The acoustic member 610 is configured by, for example, an acoustic matching layer, an acoustic lens, and the like. It performs matching of the acoustic impedance between the element chip 200 and an observation object, and it performs the convergence of the ultrasonic beam. For example, the silicon substrate of the integrated circuit devices 110, 120 is polished and thinned so that these integrated circuit devices 110, 120 are mounted on the substrate 60 of the ultrasonic transducer device 200. The acoustic member 610 is formed by, for example, a silicon resin (silicon rubber) layer, and the silicon resin layer including the integrated circuit devices 110, 120 covers a emission face of the ultrasonic transducer device 200. Because of this, the integrated circuit device 110, 120 are included in the acoustic member 610 so that the integrated circuit devices 110, 120, which were polished and thinned, are protected and it is possible for the miniaturization of the probe head.

The flexible substrates 130, 140 that were connected to the ultrasonic transducer device 200 are connected to the rigid substrate 432 by the connectors 421, 422. The rigid substrates 431 to 433 are connected by the connector 423, 424, and the integrated circuit devices 441 to 448 and the circuit elements 451 to 455 are mounted on the rigid substrates 431 to 433.

The acoustic member 610 is configured by, for example, an acoustic matching layer, an acoustic lens, and the like. It performs matching of the acoustic impedance between the element chip 200 and an observation object, and it performs the convergence of the ultrasonic beam. For example, the silicon substrate of the integrated circuit devices 110, 120 is polished and thinned so that these integrated circuit devices 110, 120 are mounted on the substrate 60 of the ultrasonic transducer device 200. The acoustic member 610 is formed by, for example, a silicon resin (silicon rubber) layer, and the silicon resin layer including the integrated circuit devices 110, 120 covers an emission face of the ultrasonic transducer device 200. Because of this, the integrated circuit device 110, 120 are included in the acoustic member 610 so that the integrated circuit devices 110, 120, which were polished and thinned, are protected and it is possible for the miniaturization of the probe head.

6. Layout Configuration of Integrated Circuit Device

Figure 11:
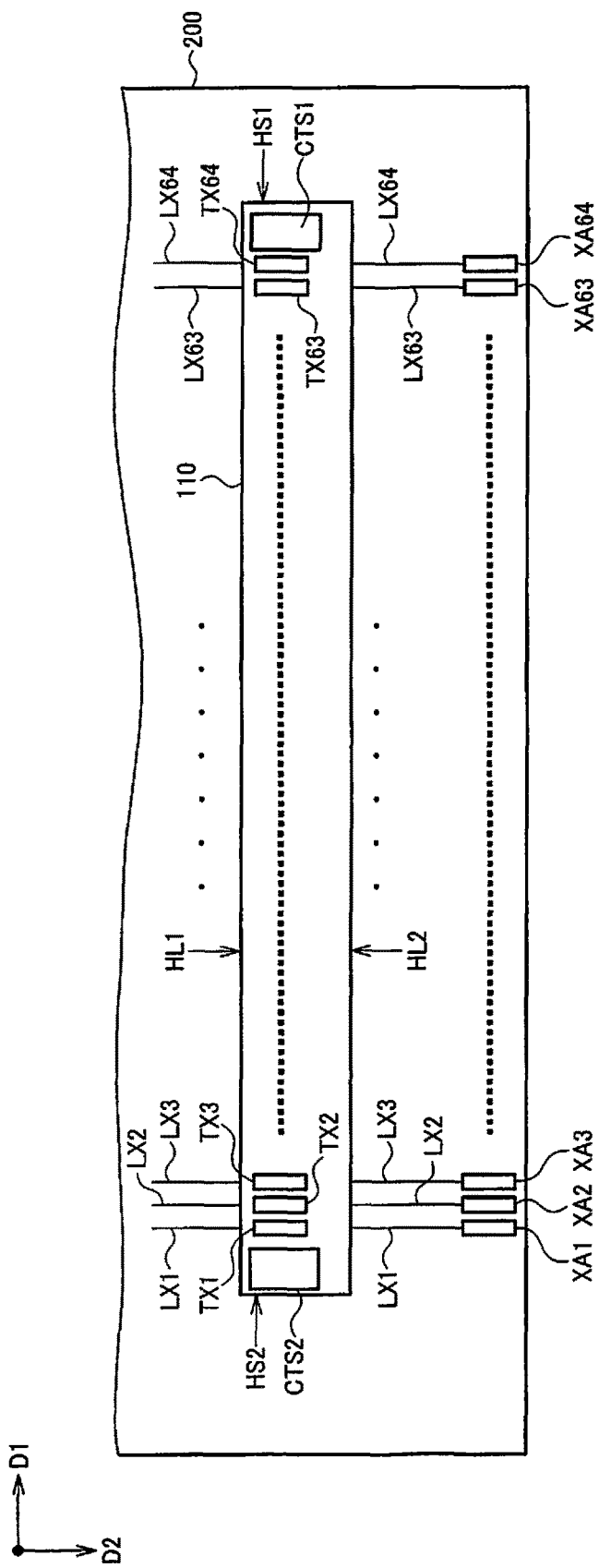
FIG. 11 is a layout configuration example of an integrated circuit device of the present embodiment.

FIG. 11 shows a layout configuration example of the integrated circuit device 110. The integrated circuit device 110 is provided with the $1^{st}$ to $64^{th}$ transmission circuits TX1 to TX64, the first control circuit CTS1, and the second control circuit CTS2. In FIG. 11, the first integrated circuit device 110 is exemplified as the layout configuration example, but the second integrated circuit device 120 can be formed in the same layout configuration.

The $1^{st}$ to $64^{th}$ transmission circuits TX1 to TX64 are arranged along the long side direction of the integrated circuit device 110. Here, the long side of the integrated circuit device 110 is the first long side HL1 and the second long side HL2. The first long side HL1 is a side opposed to the ultrasonic element array 100 at the time of mounting, and is a side where the transmission terminals TT1 to TT64 are arranged. The second long side HL2 is a side opposed to the signal terminals) CA1 to XA64 of the element chip 200 at the time of mounting, and is a side where the dummy terminals TD1 to TD64 are arranged. In such arrangement, the integrated circuit device 110 is configured in a rectangle shape elongated to the long side direction. The transmission terminals TT1 to TT64 of the integrated circuit device 110 can be opposed to the ultrasonic element array 100. Because of this, the wirings on the element chip 200 become simplified, and it is possible to configure the ultrasonic transducer device 200 in a compact size.

The first control circuit CTS1 is arranged in the first short side HS1 side of the integrated circuit device 110. Also, the second control circuit CTS2 is arranged in the second short side HS2 side of the integrated circuit device 110. The control circuits CTS1, CTS2 performs a transmission control of ultrasonic wave based on a control signal from the transmission and reception control circuit 560. Also, the control circuits CTS1, CTS2 may generate a common voltage and may supply it to the element chip 200. Because of this, by arranging the control circuits CTS1, CTS2 in the short side, the control terminals can be arranged in the short side so that the short side can be effectively utilized while keeping the elongated shape in the long side direction.

As described above, for example, in the portable type ultrasonic measurement device, and the like, there is a problem that it has a need to minimize the probe or the device main body. Also, when the drive IC of the flat package is mounted on the rigid substrate of the probe main body, there is a problem of the increase of the number of components or the costs. Further, when the area or the number of the drive IC is reduced due to the miniaturization, there is a problem that the number of channels of the ultrasonic element array is reduced.

In this point, in the present embodiment, the ultrasonic measurement device is provided with the ultrasonic transducer device 200 and the integrated circuit device 110. The ultrasonic transducer device 200 has the substrate 60, the ultrasonic element array 100 that has a plurality of ultrasonic elements 10 arranged on the substrate 60, and a plurality of signal electrode lines LX1 to LX64 that are formed on the substrate 60 and electrically connected to the ultrasonic element array 100. The integrated circuit device 110 has a plurality of terminals (plurality of transmission terminals TT1 to TT64) to output a transmission signal to the ultrasonic element array 100. Each signal electrode line of the plurality of signal electrode lines LX1 to LX64 includes an electrode layer where at least one signal electrode (the first electrode layer 21 or the second electrode layer 22) of a part of ultrasonic elements in the plurality of ultrasonic elements 10 extends on the substrate 60. The integrated circuit device 110 is mounted on the substrate 60, and each terminal of the plurality of terminals (TT1 to TT64) of the integrated circuit device 110 is connected to any of the plurality of signal electrode lines LX1 to LX64.

For example, in the present embodiment, the transmission terminal TT1 of the integrated circuit device 110 is connected to the signal electrode wire LX1 of the ultrasonic transducer device 200. That is, each terminal of the plurality of terminals (TT1 to TT64) of the integrated circuit device 110 is connected to at least one of the plurality of signal electrode lines LX1 to LX64 of the ultrasonic transducer device 200.

Accordingly, the integrated circuit device 110 is mounted on the substrate 60, and the plurality of terminals (plurality of transmission terminals TT1 to TT64) is connected to the plurality of signal electrode lines LX1 to LX64 that extends on the substrate 60. Because of this, the integrated circuit device 110 is mounted on the substrate 60 of the ultrasonic transducer device 200, and the ultrasonic element array 100 is driven by the integrated circuit device 110 so that the miniaturization of the probe head or the probe can be realized.

Further, the integrated circuit device 110 as the drive IC can be arranged on the ultrasonic transducer device 200 so that the number of components or the costs can be reduced in comparison with the case that the drive IC of the flat package is mounted on the rigid substrate of the probe main body. Further, the miniaturization can be realized without reducing the number of drive channels so that the miniaturization of the device can be realized without lowering the resolution.

By the way, in the above description, the plurality of transmission terminals, the plurality of signal wires, and the plurality of transmission circuits are described as an example that there are 64 parts, respectively, but the present embodiment is not limited to this. That is, as described in FIG. 8, etc., the number of constituent elements can be configured in various combinations in response to a scan mode that is used.

In the present embodiment, the ultrasonic element array 100 is a rectangle. When the long side direction (scan direction DS) of the rectangle is defined as the first direction D1, the integrated circuit device 110 is mounted on the substrate 60 to form the long side direction of the integrated circuit device 110 along the first direction D1. The plurality of signal electrode lines LX1 to LX64 of the substrate 60 are formed along the second direction D2 that intersects the first direction D1 on the substrate 60.

In this configuration, the integrated circuit device 110 can be arranged on the substrate 60 so as to oppose the plurality of terminals (TT1 to TT64) of the integrated circuit device 110 to the long side of the ultrasonic element array 100. Further, the opposed plurality of terminals (TT1 to TT64) and the ultrasonic element array 100 are connected by the plurality of signal electrode lines LX1 to LX64 on the substrate 60 so that the integrated circuit device 110 and the ultrasonic element array 100 can be connected in a simple wiring.

By the way, the phrase "the ultrasonic element array 100 is rectangle" is not limited to the case that the ultrasonic element array 100 is arranged to a proper rectangle such as a matrix pattern, for example. For example, it includes a case that the arrangement form of the ultrasonic element array 100 is rectangle such as a case that a part of the ultrasonic element is lacked in an inner edge part of the rectangle, or a case that a part of the ultrasonic element is exposed to the external side of outline of the rectangle.

In the bulk type ultrasonic probe head, the electrode of the piezoelectric element has a distance from the substrate so that some kind of wire member is required to connect between the terminal or the wire on the substrate and the electrode of the piezoelectric element.

In this point, in the present embodiment, as described in FIG. 1A, etc., each ultrasonic element 10 of the plurality of ultrasonic elements has the first electrode (the first electrode layer 21), the second electrode (the second electrode layer 22), and the transducer section (piezoelectric layer 30) provided between the first electrode and the second electrode. And, the first electrode or the second electrode extends on the substrate 60 as at least one signal electrode described above.

In this configuration, it is possible to simultaneously form signal electrode lines in the electrode formation process of the ultrasonic element so that it is possible to connect from the electrodes of the transducer section to the signal terminals XA1 to XA64 of the element chip 200 by the signal electrode lines that were extendedly formed on the substrate 60 without providing other wire member. Because of this, the configuration of the probe head is simplified, and the probe head can be minimized. Also, the manufacturing process of the ultrasonic transducer device 200 can be simplified.

By the way, the ultrasonic element, which is a type of using the piezoelectric element, is described as an example in the present embodiment, but the present embodiment is not limited to this. For example, a transducer, which is a type of using capacitive device such as the Capacitive Micromachined Ultrasonic transducers (c-MUT), and the like, may be employed as an ultrasonic element.

Further, in the present embodiment, the integrated circuit device 110 has the transmission circuits TX1 to TX64 to output a transmission signal in each of the plurality of terminals (TT1 to TT64). The plurality of transmission circuits TX1 to TX64 is arranged along the first direction D1 in the state that the integrated circuit device 110 is mounted on the substrate 60.

In this configuration, it is possible to configure the integrated circuit device 110 in an elongated-shape by arranging the plurality of transmission circuits TX1 to TX64 along the first direction D1. Because of this, the integrated circuit device 110 can be mounted on the substrate 60 so as to oppose the plurality of transmission circuits TX1 to TX64 to the ultrasonic element array 100. Also, the opposed plurality of transmission circuits TX1 to TX64 and the ultrasonic element array 100 are connected by the wiring on the substrate 60 so that the miniaturization of the probe head or the probe can be realized.

7. Second Basic Configuration of Ultrasonic Measurement Device

In the above description, it is described in the case that the integrated circuit device 110 includes the transmission circuits TX1 to TX64, but the present embodiment is not limited to this so that the integrated circuit device 110 further includes a switch element and a multiplexer. In the followings, the configuration example of the ultrasonic measurement device will be described in this case. In the followings, the first integrated circuit device 110 will be described as an example, but the second integrated circuit device 120 can be configured in the same manner.

Figure 12:
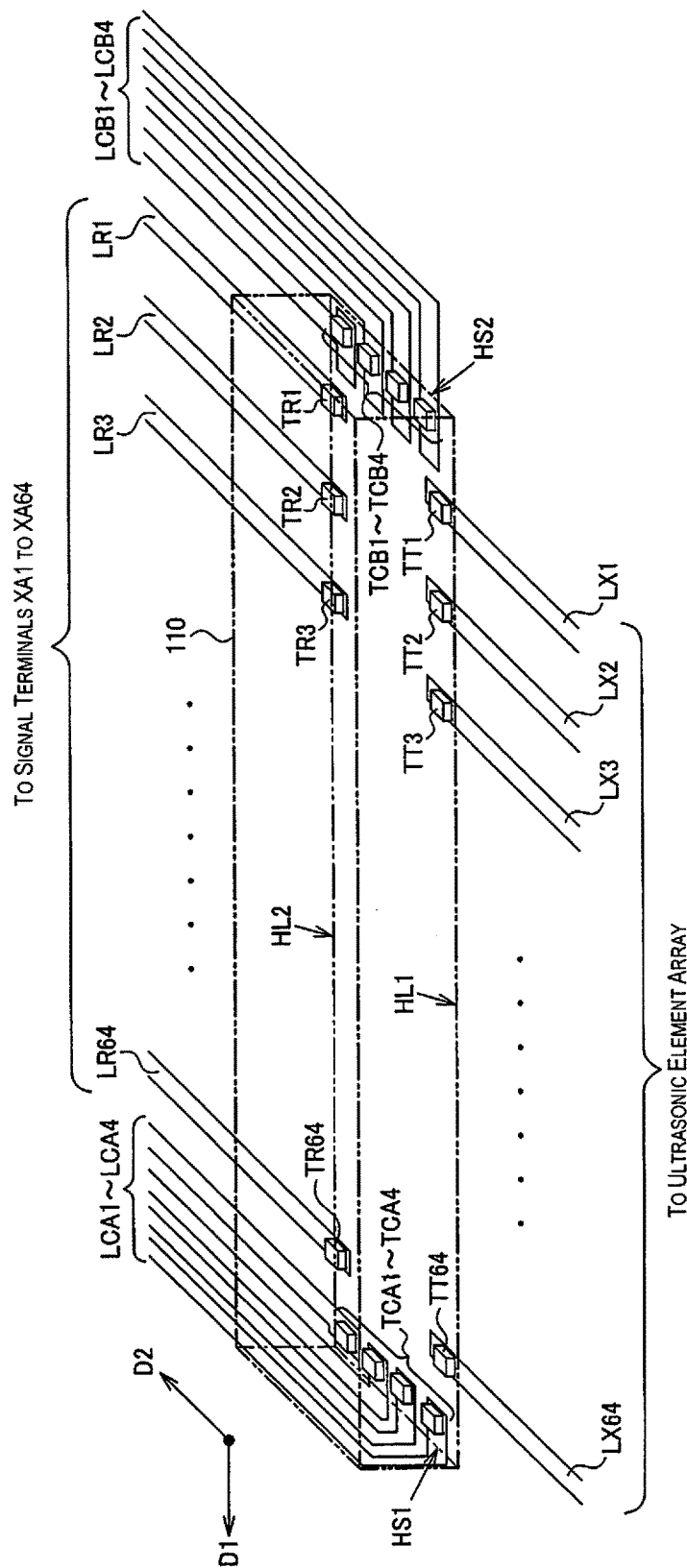
FIG. 12 is a basic configuration example of an ultrasonic measurement device of the present embodiment.

FIG. 12 shows the second basic configuration of an ultrasonic measurement device. As shown in FIG. 12, in the substrate 60 of the ultrasonic transducer device 200, the signal electrode lines LX1 to LX64 (plurality of signal electrode lines) are wired along the second direction D2. Also, in the substrate 60, the $1^{st}$ to $64^{th}$ reception signal wires LR1 to LR64 (plurality of reception signal wires) are wired along the second direction D2.

In the integrated circuit device 110, the $1^{st}$ to $64^{th}$ transmission and reception terminals TT1 to TT64 (plurality of transmission and reception terminals) are arranged along the first long side HL1 of the integrated circuit device 110, and the $1^{st}$ to $64^{th}$ reception signal output terminals TR1 to TR64 (plurality of reception signal output terminals) are arranged along the second long side HL2 of the integrated circuit device 110. Also, in the integrated circuit device 110, the control terminals TCA1 to TCA4, TCB1 to TCB4 can be arranged along the first short side HS1, the second short side HS of the integrated circuit device 110. These terminals are a bump terminal, and for example, it is formed by applying metal plating to a pad terminal of the integrated circuit device 110. Alternatively, a resin layer that becomes as an insulating layer, a metal wire, and a bump terminal that is connected to the metal wire may be formed on the element formation surface of the integrated circuit device 110.

The integrated circuit device 110 is mounted on the substrate 60 of the ultrasonic transducer device 200 so as to form the long side along the first direction D1. At the time of mounting, the $1^{st}$ to $64^{th}$ transmission and reception terminals TT1 to TT64 of the integrated circuit device 110 are connected to one end of the $1^{st}$ to $64^{th}$ signal electrode lines LX1 to LX64. Also, the $1^{st}$ to $64^{th}$ reception signal output terminals TR1 to TR64 of the integrated circuit device 110 are connected to one end of the $1^{st}$ to $64^{th}$ reception signal wires LR1 to LR64. In the other end of the $1^{st}$ to $64^{th}$ reception signal wires LR1 to LR64, the $1^{st}$ to $64^{th}$ signal terminals XA1 to XA64 of the ultrasonic transducer device 200 are connected.

At the time of mounting, the control terminals TCA1 to TCA4, TCB1 to TCB4 are connected to the control signal wires LCA1 to LCA4, LCB1 to LCB4 of the substrate 60. For example, a transmission pulse signal or a transmission and reception control signal is supplied to the control signal wires LCA1 to LCA4, LCB1 to LCB4 from the transmission and reception signal control circuit 560 in FIG. 13A, and the integrated circuit device 110 generates a transmission signal based on a transmission pulse signal or a transmission and reception control signal and performs a transmission and reception switching control. Also, it is not shown in the drawing, but a common output terminal may be provided in the integrated circuit device 110. The common output terminal supplies a common voltage to a common terminal XAC of the element chip 200 in FIG. 2 through a wire on the flexible substrate 130.

Next, the operation of the second basic configuration example as described above will be described. The integrated circuit device 110 outputs a transmission signal to the ultrasonic element array 100 through the $1^{st}$ to $64^{th}$ transmission and reception terminals TT1 to TT64 and the $1^{st}$ to $64^{th}$ signal electrode lines LX1 to LX64. The ultrasonic element array 100 emits the ultrasonic wave by the transmission signal and the ultrasonic wave is reflected from an observation object so that the reflection wave is received by the ultrasonic element array 100. The reception signal generated by receiving the reflection wave is inputted to the integrated circuit device 110 through the $1^{st}$ to $64^{th}$ signal electrode lines LX1 to LX64 and the $1^{st}$ to $64^{th}$ transmission and reception terminals TT1 to TT64, and it is outputted to the latter part of the reception circuit (e.g., analog front end circuit 550 in FIG. 13A) through the $1^{st}$ to $64^{th}$ reception signal output terminals TR1 to TR64 and the $1^{st}$ to $64^{th}$ reception signal wires LR1 to LR64.

8. Second Detailed Configuration of Ultrasonic Measurement Device

Figure 13A:
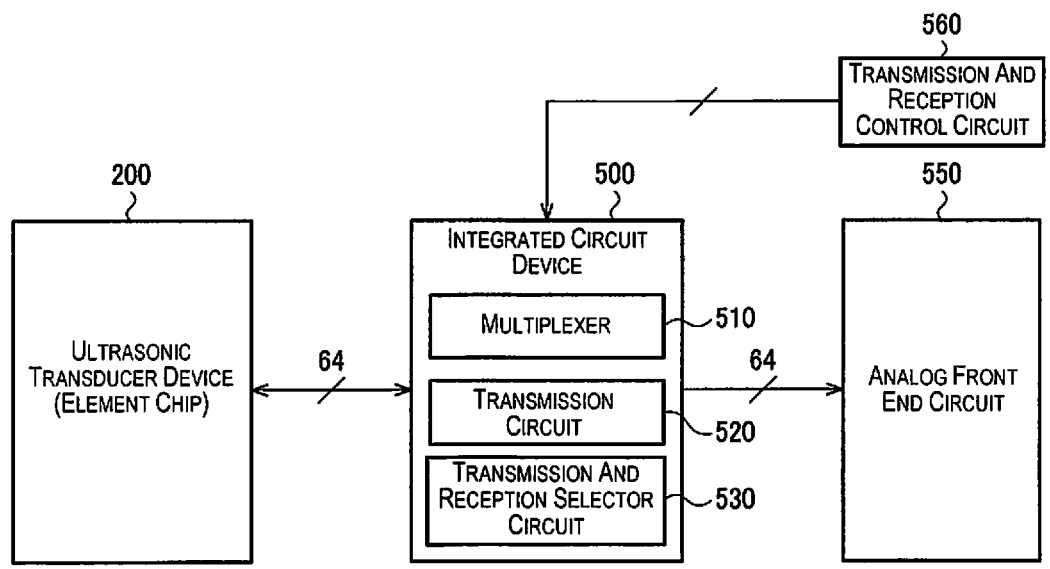
FIG. 13A and FIG. 13B are a circuit block diagram of a second configuration example of an ultrasonic measurement device of the present embodiment.

FIG. 13A shows a circuit block diagram of a configuration example of an ultrasonic measurement device. The ultrasonic measurement device is provided with the element chip 200, the integrated circuit device 500, the analog front end circuit 550, and the transmission and reception control circuit 560. By the way, in the followings, the case that integrated circuit device 500 corresponds to the first integrated circuit device 110 will be described as an example, but the integrated circuit device 500 may correspond to the second integrated circuit device 120, or may include both of the first integrated circuit device 110 and the second integrated circuit device 120.

The transmission and reception control circuit 560 performs a transmission control or a reception control of the ultrasonic wave for the integrated circuit device 500. The transmission and reception control circuit 560 supplies these control signals to the control signal wires LCA1 to LCA4, LCB1 to LCB4 and the control terminals TCA1 to TCA4, TCB1 to TCB4 through the integrated circuit device 500.

In the analog front end circuit 550, a reception signal is inputted from the element chip 200 through the integrated circuit device 500, and the analog front end circuit 550 performs a reception processing such as, for example, an amplification processing, an A/D converting processing, and the like according to the reception signal.

The integrated circuit device 500 is provided with the transmission circuit 520 that amplifies a transmission pulse signal from the transmission and reception control circuit 560, the multiplexer 510 that performs a transmission control of a transmission signal from the transmission circuit 520 and a reception control of a reception signal from the element chip 200, and the transmission and reception signal selector circuit 530 that outputs a reception signal from the multiplexer 510 to the analog front end circuit 550.

Figure 14:
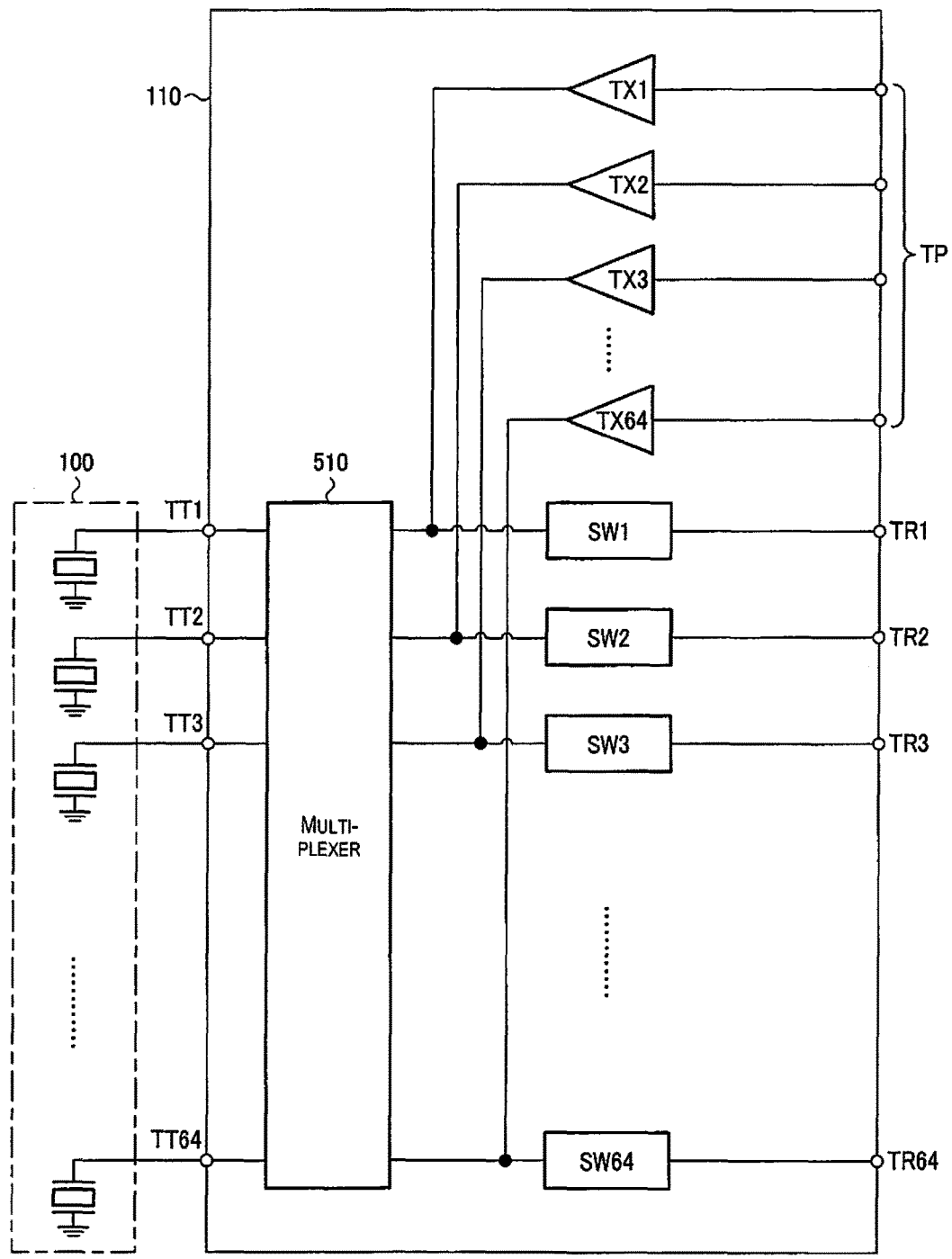
FIG. 14 is a second detailed configuration example of an integrated circuit device of the present embodiment.

FIG. 14 shows a detailed configuration example of the integrated circuit device 110 corresponding to the integrated circuit device 500. The integrated circuit device 110 is provided with the multiplexer 510, the $1^{st}$ to $64^{th}$ transmission circuits TX1 to TX64, and the $1^{st}$ to $64^{th}$ switch elements SW1 to SW64 (plurality of transmission and reception selector switches).

In the transmission period of the ultrasonic wave, the transmission and reception control circuit 560 supplies a transmission pulse signal to the $1^{st}$ to $64^{th}$ transmission circuits TX1 to TX64 through the terminal group TP. Here, the terminal group TP is the terminals included in the control terminals TCA1 to TCA4 in FIG. 12. The $1^{st}$ to $64^{th}$ transmission circuit TX1 to TX64 amplifies the supplied transmission pulse signal and outputs to the multiplexer 510. The multiplexer 510 outputs the amplified transmission pulse signal to the ultrasonic element array 100 through the $1^{st}$ to $64^{th}$ transmission and reception terminals TT1 to TT64.

In the transmission period of the ultrasonic wave, the $1^{st}$ to $64^{th}$ switch element SW1 to SW64 are turned off based on the instruction from the transmission and reception control circuit 560, and a transmission pulse signal from the $1^{st}$ to $64^{th}$ transmission circuits TX1 to TX64 is not outputted to the analog front end circuit 550. The analog front end circuit 550 is operated in approximately few voltages in general so that the transmission pulse signal is blocked in order to avoid breaking by the transmission pulse signal that has the amplitude of approximately 10 to 30V.

In the reception period of the ultrasonic wave, the ultrasonic element array 100 receives the reflection wave of the ultrasonic wave from an observation object, and the reception signal is inputted to the $1^{st}$ to $64^{th}$ transmission and reception terminals TT1 to TT64 through the multiplexer 510. The multiplexer 510 outputs the reception signal to the $1^{st}$ to $64^{th}$ switch elements SW1 to SW64. The $1^{st}$ to $64^{th}$ switch elements SW1 to SW64 are turned on in the reception period of the ultrasonic element array 100, and a reception signal is outputted to the analog front end circuit 550 through the $1^{st}$ to $64^{th}$ reception signal output terminals TR1 to TR64.

In the case of performing the phase scan, the multiplexer 510 can be provided with a phase control circuit (delay circuit) that performs the phase scan of the transmission signal and a reception signal. Specifically, the phase control circuit delays a transmission pulse signal from the $1^{st}$ to $64^{th}$ transmission circuits TX1 to TX64 based on the instruction from the transmission and reception circuit 560, and performs the phase scan of the ultrasonic beam. Here, the phase scan means to control the phase difference between the transmission signals, and to scan in an emitting direction (beam direction) of the ultrasonic wave. And, during the reception period, the phase control circuit delays the reception signal according to the phase difference between the transmission signals so as to output to the analog front end circuit 550 by matching the phase of the reception signals.

In the case of performing the linear scan, the multiplexer 510 performs the switching control of transmission or reception based on the instruction from the transmission and reception control circuit 560. Specifically, as an example of a linear scan that drives 8 channels at once, the $1^{st}$ to $8^{th}$ transmission circuits TX1 to TX8 output a transmission pulse signal in the transmission period. The $9^{th}$ to $64^{th}$ transmission circuits TX9 to TX64 are set for non-operational mode (e.g., power-save mode or power-down mode). And, the multiplexer 510 outputs eight transmission pulse signals to the $1^{st}$ to $8^{th}$ transmission and reception terminals TT1 to TT8 during the first transmission period and outputs it to the $2^{nd}$ to $9^{th}$ transmission and reception terminals TT2 to TT9 during the second transmission period. Accordingly, the ultrasonic element array 100 is driven by sequentially shifting the ultrasonic element rows that are driven.

At the time of receiving, first, the reception signal is inputted from the $1^{st}$ to $8^{th}$ transmission and reception terminals TT1 to TT8 during the first reception period. Next, the reception signal is inputted from the $2^{nd}$ to $9^{th}$ transmission and reception terminals TT2 to TT9 during the second reception period. Accordingly, the ultrasonic wave is received by sequentially shifting the ultrasonic element rows. And, the multiplexer 510 outputs the eight reception signals to the $1^{st}$ to $8^{th}$ switch elements SW1 to SW8. The $1^{st}$ to $8^{th}$ switch elements SW1 to SW8 are turned on and the $9^{th}$ to $64^{th}$ switch elements SW9 to SW64 are turned off.

Figure 13B:
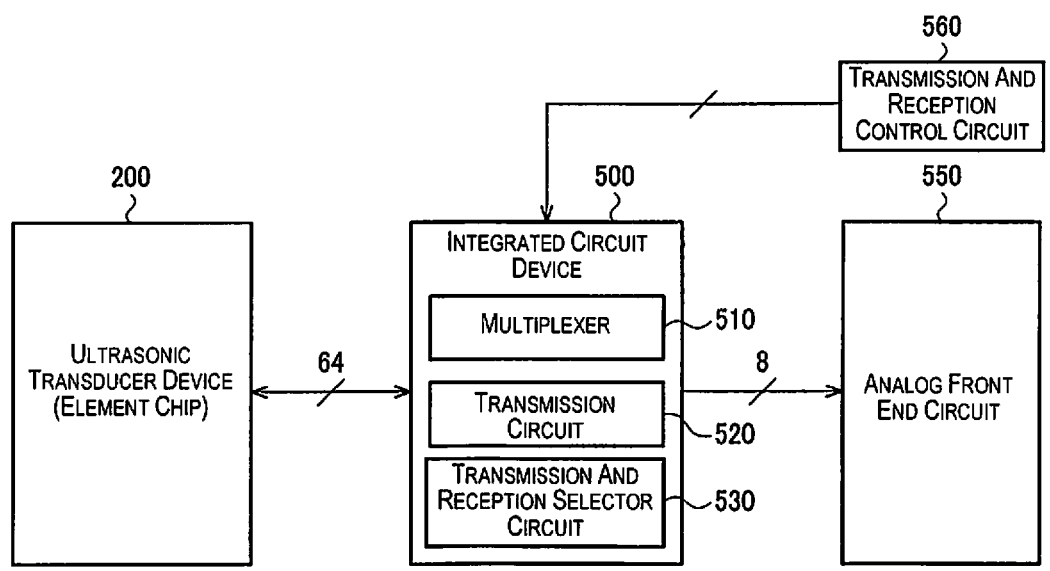

By the way, in the ultrasonic measurement device of FIG. 13A, it may be a configuration that it does not perform the linear scan and it only performs the phase scan. Also, in the present embodiment, the ultrasonic measurement device may perform only the linear scan. FIG. 13B is a block diagram of a configuration example of the ultrasonic measurement device in the case of performing only a linear scan. The ultrasonic measurement device is provided with the element chip 200, the integrated circuit device 500, the analog front end circuit 550, and the transmission and reception control circuit 560. The integrated circuit device 500 is provided with the 1st to 8th transmission circuits TX1 to TX8 as a transmission circuit TX, and the 1st to 8th switch elements SW1 to SW8 as a transmission and reception selector circuit 530. And, the 1st to 8th transmission circuits TX1 to TX8 output a transmission signal at the time of the transmission, and the multiplexer 510 scans the transmission channel. At the time of the reception, the multiplexer 510 scans the reception channel, and the 1st to 8th switch elements SW1 to SW8 output a reception signal to the analog front end circuit 550.

Accordingly, in the ultrasonic measurement device of the present embodiment, various combinations of the number of the transmission circuit or the switch elements (and, the number of terminals corresponding to it) can be configured in response to the scan mode, the number of drive channels, the number of reception channels, and the like.

Also, in the present embodiment, the multiplexer 510 may be omitted. In this case, in the case of performing the phase scan, the transmission and reception control circuit 560 controls to delay a transmission pulse signal, the transmission pulse signal having a phase difference is supplied to the 1st to 64th transmission circuits TX1 to TX64. At the time of the reception, the analog front end circuit 550 performs a delay control in response to the phase difference of the reception signal. Also, in the case of performing the linear scan, the 1st to 8th transmission circuits TX1 to TX8 send during the first transmission period, and next, the 2nd to 9th transmission circuits TX2 to TX9 send during the second transmission period. Accordingly, the transmission circuits that output a transmission signal are sequentially shifted. And, at the time of the reception, the 1st to 8th switch elements SW1 to SW8 are turned on during the first reception period, and next, the 2nd to 9th switch elements SW2 to SW8 are turned on during the second reception period. Accordingly, the switch elements to be turned on are sequentially switched over.

9. Second Layout Configuration of Integrated Circuit Device

Figure 15:
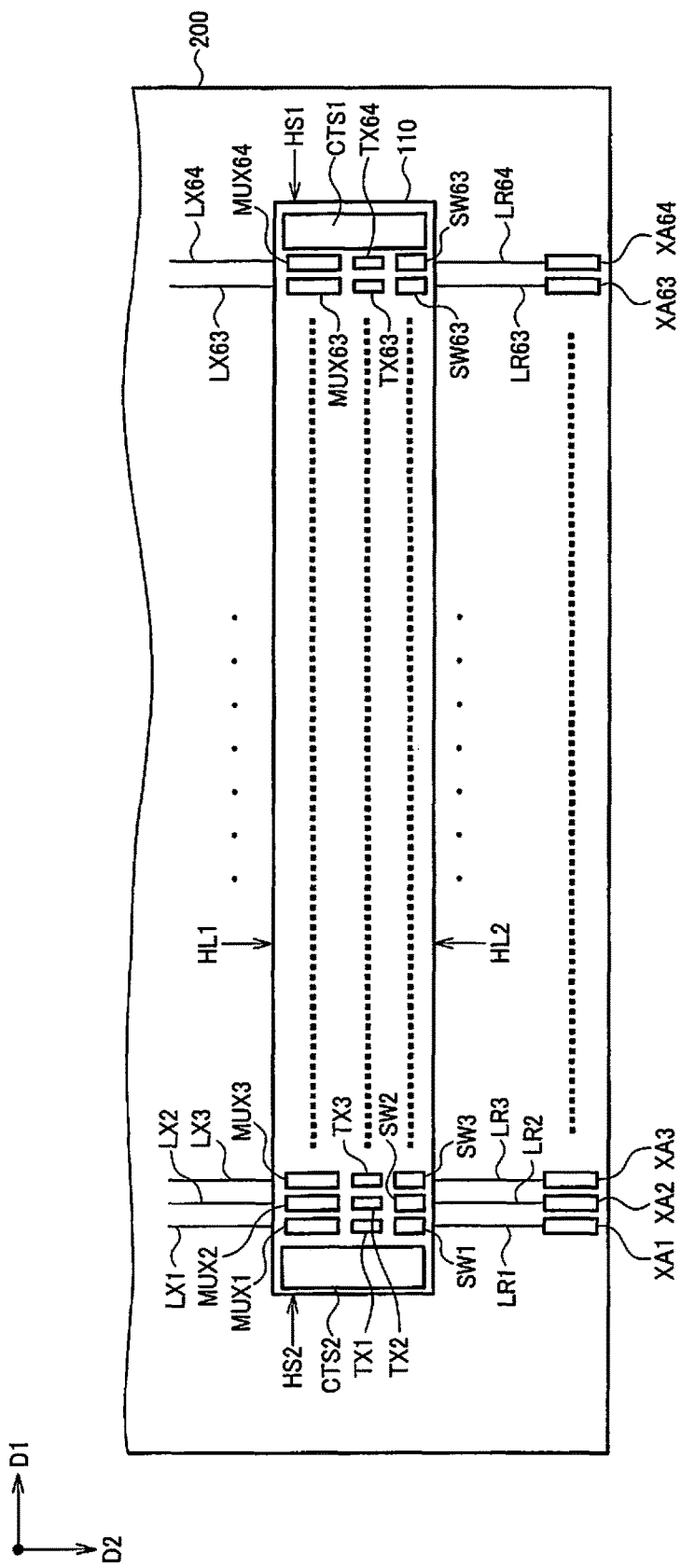
FIG. 15 is a second layout configuration example of an integrated circuit device of the present embodiment.

FIG. 15 is a second layout configuration example of the integrated circuit device 110. The integrated circuit device 110 is provided with the 1st to 64th multiplexers MUX1 to MUX64, the 1st to 64th transmission circuits TX1 to TX64, the 1st to 64th switch elements SW1 to SW64, the first control circuit CTS1, and the second control circuit CTS2.

The 1st to 64th multiplexer MUX1 to MUX64 are arranged along the first long side HL1 of the integrated circuit device 110. The first long side HL1 is a side opposed to the signal terminals XA1 to XA64 of the element chip 200 at the time of mounting, and the transmission and reception terminals TT1 to TT64 are arranged in the side. By the way, the 1st to 64th multiplexers MUX may be converted to a cell and arranged as shown in FIG. 15, or it may be formed as an integrated circuit block. In the case of forming the integrated circuit block, the long side of the circuit block is arranged along the first long side HL1. By forming this arrangement, the 1st to 64th multiplexers MUX1 to MUX64 can be arranged in near position with respect to the transmission and reception terminals TT1 to TT64 so that the efficient layout can be realized.

The 1st to 64th switch elements SW1 to SW64 are arranged along the second long side HL2 of the integrated circuit device 110. The second long side HL2 is a side where the reception signal output terminals TR1 to TR64 are arranged. The 1st to 64th switch elements SW1 to SW64 are converted to a cell and arranged as shown in FIG. 15. By forming this arrangement, the 1st to 64th switch elements SW1 to SW64 can be arranged in a position near with respect to the reception signal output terminals TR1 to TR64 so that the efficient layout can be realized.

The 1st to 64th transmission circuits TX1 to TX64 are arranged along the long side direction between the 1st to 64th multiplexers MUX1 to MUX64 and the 1st to 64th switch elements SW1 to SW64. The 1st to 64th transmission circuits TX1 to TX64 are converted to a cell and arranged as shown in FIG. 15.

The first control circuit CTS1 is arranged in the first short side HS1 of the integrated circuit device 110. Also, the second control circuit CTS2 is arranged in the second short side HS2 side of the integrated circuit device 110. The control circuits CTS1, CTS2 perform the transmission and reception signal control based on a control signal from the transmission and reception control circuit 560. Also, the control circuits CTS1, CTS2 may generate a common voltage and supply it to the ultrasonic element array 100. Because of this, by arranging the control circuits CTS1, CTS2 in the short sides, the control terminal can be arranged in the short side so that the short sides can be efficiently utilized while maintaining the elongated shape in the long side direction.

As described above embodiment, the integrated circuit device 110 has a transmission and reception selector switch (switch elements SW1 to SW64) that connects to the corresponding terminal in each of the plurality of terminals (plurality of transmission and reception terminals TT1 to TT64) of the integrated circuit device 110. The plurality of transmission and reception selector switches is arranged along the first direction D1 in the state that the integrated circuit device 110 is mounted on the substrate 60.

Accordingly, the integrated circuit device 110 has the plurality of transmission and reception selector switches (switch elements SW1 to SW64) so that the transmission signal from the transmission circuits TX1 to TX64 is suppressed to input to the reception circuit, and it is possible to protect the reception circuit from the electric breakdown. Also, by arranging the plurality of transmission and reception selector switches (switch elements SW1 to SW64) along the first direction D1, it can be efficiently arranged with layout with respect to the elongated integrated circuit device 110.

Also, the present embodiment, the integrated circuit device 110 is provided with the multiplexers MUX1 to MUX64 (or 510). The multiplexer MUX1 to MUX64 are provided between the plurality of terminals (TT1 to TT64) arranged along the first direction D1 and the plurality of transmission circuits TX1 to TX64 arranged along the first direction D1.

Accordingly, it arranges in order of the plurality of transmission circuits TX1 to TX64, the multiplexer MUX1 to MUX64, and the plurality of terminals (TT1 to TT64) so that it can be the circuit arrangement along the flow of the signal.

Also, in the present embodiment, the integrated circuit device 110 has the plurality of reception signal output terminals TR1 to TR64. Each reception signal output terminal of the plurality of reception signal output terminals TR1 to TR64 is connected to any of the plurality of transmission and reception selector switches (switch elements SW1 to SW64). The plurality of terminals (TT1 to TT64) is arranged along the first long side HL1 of the integrated circuit device 110, and the plurality of reception signal output terminals TR1 to TR64 is arranged along the second long side HL2 which is opposed to the first long side HL1.

Accordingly, the plurality of terminals (TT1 to TT64) is arranged opposing to the ultrasonic element array 100 in the state that the integrated circuit device 110 is mounted on the substrate 60, and the plurality of reception signal output terminals TR1 to TR64 can be arranged in the opposite side. Because of this, the terminals can be arranged along the flow of signal in the transmission and reception of the ultrasonic wave.

10. Head Unit

Figure 16:
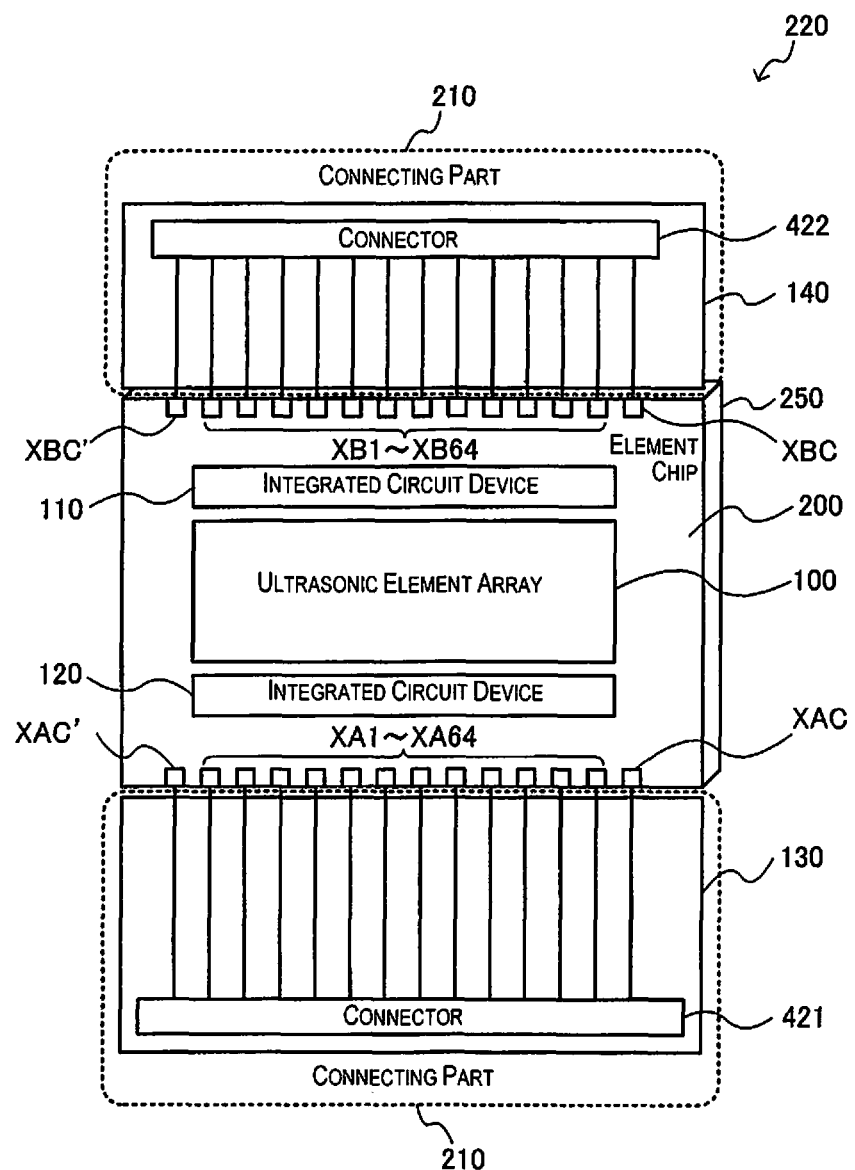
FIG. 16 is a configuration example of a head unit.

FIG. 16 is a configuration example of the head unit 220 in which the ultrasonic measurement device of the present embodiment is mounted. The head unit 220 shown in FIG. 16 is provided with the element chip 200, a connecting part 210, and a support member 250. By the way, the head unit 220 of the present embodiment is not limited to the configuration of FIG. 16 so that it may be possible to provide various modified embodiments such that a part of the configuration elements may be omitted or replaced to other configuration elements, or other configuration elements may be added.

The element chip 200 corresponds to the ultrasonic transducer device described in FIG. 2. The element chip 200 is provided with the ultrasonic element array 100, the first chip element group XA1 to XA64 (plurality of signal terminals), the second chip terminal group XB1 to XB64 (second plurality of signal terminals), and the common terminals XAC, XBC. As described in FIG. 2, the common electrode wire LXC is connected to one end of the common electrode wires LY1 to LY8, and the common terminals XAC, XBC are connected to both ends of the common electrode wire LXC. Also, the element chip 200 can be provided with the common terminals XAC', XBC'. The common terminals XAC', XBC' are connected to both ends of the common electrode wires, which are not shown and are connected to the other end of the common electrode wires LY1 to LY8. In the element chip 200, the integrated circuit devices 110, 120 are subjected to flip chip mounting. The element chip 200 is electrically connected with a processing device (e.g., processing device 330 of FIG. 19) that is provided in the probe main body through the connecting part 210.

The connecting part 210 is to connect between the probe main body and the head unit 220, electrically, and is provided with a connector having a plurality of connecting terminals, and a flexible substrate forming a wire that connects between the connector and the element chip 200. Specifically, the connecting part 210 has the first connector 421 and the second connector 422 as a connector, and has the first flexible substrate 130 and the second flexible substrate 140 as a flexible substrate.

In the first flexible substrate 130, the first chip terminal group XA1 to XA64 provided in the first side of the element chip 200 and the first wire group (plurality of signal wires) connected with the terminal group of the connector 431 are formed.

In the flexible substrate 140, the second chip terminal group XB1 to XB64 (second plurality of signal terminals) provided in the second side of the element chip 200 and the second wire group (second plurality of signal wires) connected with the terminal group of the connector 422 are formed.

The connector 421 has a plurality of connecting terminals in which a reception signal from the first chip terminal group XA1 to XA64 is outputted through the first wire group formed on the flexible substrate 130. The connector 422 has a plurality of connecting terminals in which a reception signal from the second chip terminal group XB1 to XB64 is outputted through the second wire group formed on the flexible substrate 140.

By the way, the connecting part 210 is not limited to the configuration shown in FIG. 16. The connecting part 210 may have the first connecting terminal group in which a reception signal from the first chip terminal group provided in the first side of the element chip 200 is outputted, and the second connecting terminal group in which a reception signal from the second chip terminal group provided in the second side of the element chip 200 is outputted.

By providing the connecting part 210, the probe main body and the head unit 220 can be electrically connected, and in addition, the head unit 220 can be detachable from the probe main body.

The support member 250 is a member that supports the element chip 200, and as described later, a plurality of connecting terminals is provided in the first surface side of the support member 250, and the element chip 200 is supported in the second surface side which is the back surface of the first surface of the support member 250. By the way, the specific configuration of the element chip 200, the connecting part 210 and the support member 250 will be described later.

FIG. 17A to 17C show detailed configuration examples of the head unit 220. FIG. 17A shows the second surface SF2 side of the support member 250. FIG. 17B shows the first surface SF1 side of the support member 250. FIG. 17C shows the side face side of the support member 250. By the way, the head unit 220 of the present embodiment is not limited to the configurations of FIG. 17A to FIG. 17C so that it may be possible to provide various modified embodiments such that a part of the configuration elements may be omitted or replaced to other configuration elements, or other configuration elements may be added.

In the first surface SF1 side of the support member 250, the connectors 421, 422 (broadly, plurality of connecting terminals) are provided. The one ends of the flexible substrates 130, 140 are respectively connected to the connectors 421, 422. The connectors 421, 422 are detachable from a connector corresponding to the probe main body side.

In the second surface SF2 side that is the back surface of the first surface SF1 of the support member 250, the element chip 200 is supported. The other ends of the flexible substrates 130, 140 are connected to the terminal of the element chip 200. The fixing member 260 is provided in each corner section of the support member 250, and it is used to fix the head unit 220 in the probe case.

Here, the first surface side of the support member 250 is a normal direction side of the first surface SF1 of the support member 250, and the second surface side is a normal direction side of the second surface SF2 that is the back surface of the first surface SF1 of the support member 250.

As shown in FIG. 17C, a protection member (protection film) 270 that protects the element chip 200 is provided on the surface of the element chip 200 (the surface forming the piezoelectric layer 30 in FIG. 1B). The integrated circuit devices 110, 120 are mounted on the element chip 200, and the integrated circuit devices 110, 120 together with the surface of the element chip 200 is covered by the protection member 270.

11. Ultrasonic Probe

Figure 18A:
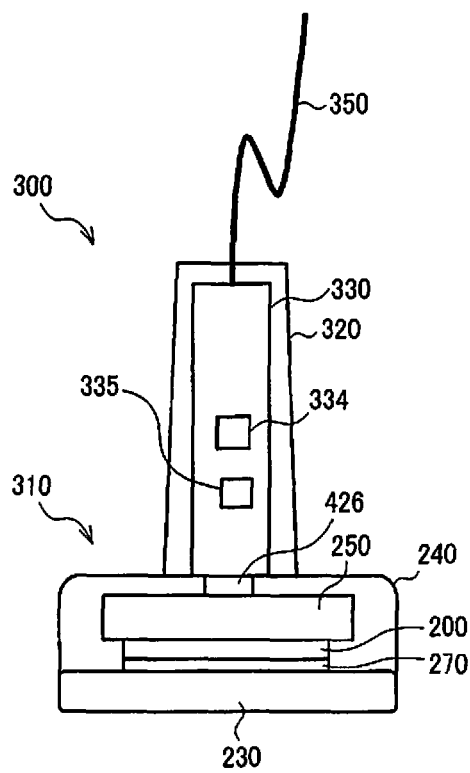
FIG. 18A and FIG. 18B are a configuration example of an ultrasonic probe.
Figure 18B:
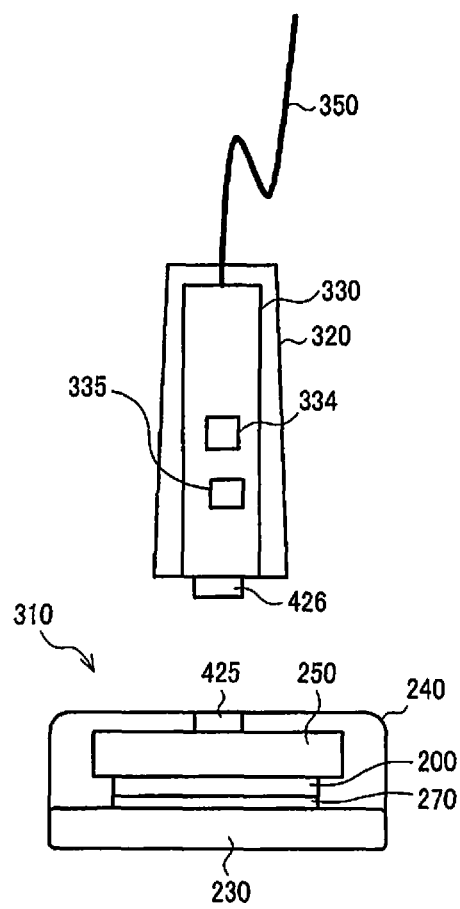

FIG. 18A and FIG. 18B show configuration examples of an ultrasonic probe 300 that the above head unit 220 is applied. FIG. 18A shows the case that the probe head 310 is mounted on the probe main body 320, and FIG. 18B shows the case that the probe head 310 is separated from the probe main body 320.

The probe head 310 is provided with the head unit 220, and the probe case 240 that stores a contact member 230, which contacts to a subject, and the head unit 220. The element chip 200 is provided between the contact member 230 and the support member 250.

The probe main body 320 is provided with a processing device 330 and a probe main body side connector 426. The processing device 330 is provided with a reception section 335 (analog front end section) and a transmission and reception control section 334. The reception section 335 performs a reception processing of an ultrasonic echo signal (reception signal) from the ultrasonic transducer element. The transmission and reception control section 334 performs to control the integrated circuit devices 110, 120, and the reception section 335. The probe main body side connector 426 is connected to the head unit (or probe head) side connector 425. The probe main body 320 is connected to an electronic equipment (e.g., ultrasonic diagnostic device) by a cable 350.

The head unit 220 is stored in the probe case 240, but the head unit 220 can be removed from the probe case 240. Accordingly, only the head unit 220 can be replaced. Alternatively, in the state that it is stored in the probe case 240, that is, it can be replaced as the probe head 310.

12. Ultrasonic Diagnostic Device

Figure 19:
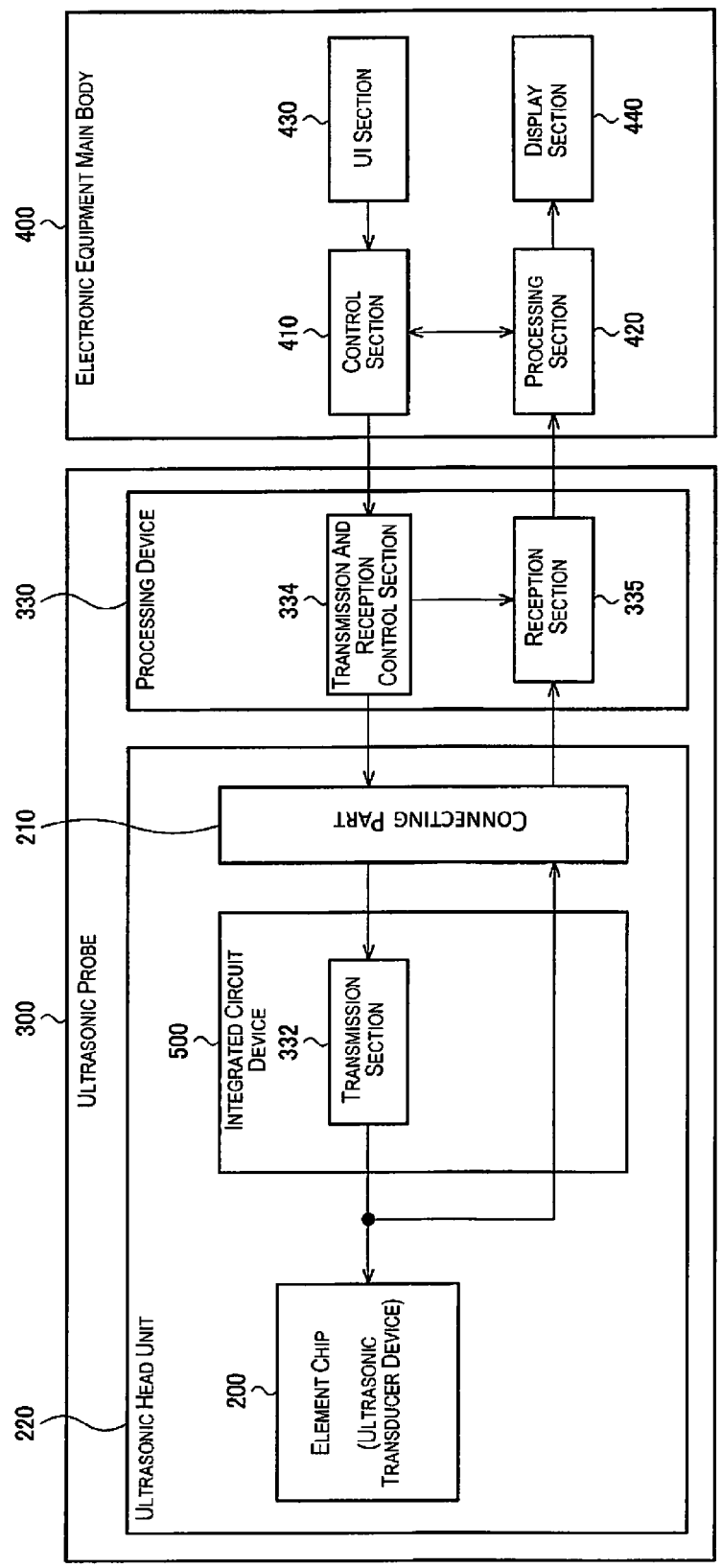
FIG. 19 is a configuration example of an ultrasonic diagnostic device.

FIG. 19 shows a configuration example of an ultrasonic diagnostic device. The ultrasonic diagnostic device is provided with an ultrasonic probe 300 and an electronic equipment main body 400. The ultrasonic probe 300 is provided with an ultrasonic head unit 220 and a processing device 330. The electronic equipment main body 400 is provided with a control section 410, a processing section 420, a user interface section 430, and a display section 440.

The processing device 330 is provided with a transmission and reception control section 334 and a reception section 335 (analog front end section). The ultrasonic head unit 220 is provided with the element chip 200 (ultrasonic transducer device), an integrated circuit device 500 that is mounted on the element chip 200, and a connecting part 210 (connector section) in which the element chip 200 connects with a circuit substrate (e.g., rigid substrate). In the circuit substrate, the transmission and reception control section 334 and the reception section 335 are mounted. The integrated circuit device 500 is provided with the transmission section 332.

In the case of transmitting an ultrasonic wave, the transmission and reception control section 334 performs to instruct the transmission section 332 for a transmission, and the transmission section 332 receives the transmission instruction and amplifies the drive signal at a high voltage so as to output the drive voltage. The transmission section 335 has a limiter circuit, which is not shown, and the limiter circuit blocks the drive voltage. In the case of receiving the reflection wave of the ultrasonic wave, the reception section 335 receives the signal of the reflection wave detected by the element chip 200. The reception section 335 processes the signal of the reflection wave (e.g., amplification process, or A/D converting process, and the like) based on the reception instruction from the transmission and reception control section 334, and the signal that was processed is sent to the processing section 420. The signal creates an image and it is displayed in the display section 440.

By the way, the ultrasonic measurement device of the present embodiment is not limited to the ultrasonic diagnostic device for medical equipment as described above so that it is possible to apply for various types of electronic equipment. For example, as electronic equipment in which the ultrasonic transducer device is applied, a diagnostic equipment that non-destructively detects inside of a building, and the like, or a user interface equipment that detects the movement of user's fingers by the reflection of ultrasonic wave may be assumed.

By the way, the present embodiments were described above in detail, but it will be apparent to those skilled in the art that various modifications can be made in a scope not substantially deviating from the subject matter and the effect of the present invention. Therefore, such changes and modifications are included in the scope of the invention. For example, the terms used in the specification or the drawings at least once together with a different term having a broader or similar meaning can be replaced with the different term in any portion of the specification or the drawings. Also, the present embodiment and all of the combinations of the modification examples are included in the scope of the present invention. In addition, the integrated circuit device, the ultrasonic element, the configurations/operations of the ultrasonic transducer device, the ultrasonic head unit, the ultrasonic probe, the ultrasonic diagnostic device, the mounting means of the integrated circuit device, the scanning means of the ultrasonic beam, and the like are not limited to the described present embodiment so that various modifications can be possible.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic measurement device comprising:
  an ultrasonic transducer device including
    a substrate, an ultrasonic element array having a plurality of ultrasonic elements arranged on a surface of the substrate, a plurality of signal electrode lines formed on the surface of the substrate and electrically connected to the ultrasonic element array, each of the signal electrode lines extending in one direction along a slice direction and the surface of the substrate, and including an electrode layer in which at least one signal electrode among some of the ultrasonic elements is formed to extend in the one direction on the surface of the substrate, each of the signal electrode lines further including a signal terminal at one end portion of each of the signal electrode lines, the one end portion being positioned, relative to all of the ultrasonic elements, in the one direction, and an integrated circuit device having a plurality of terminals to output a transmission signal to the ultrasonic element array, the integrated circuit device being mounted on the surface of the substrate such that the integrated circuit device does not overlap all of the ultrasonic elements and the signal terminal of each of all of the signal electrode lines as viewed in a direction perpendicular to the surface of the substrate, and such that the entire integrated circuit device is arranged between the all of the ultrasonic elements and the signal terminal of each of all of the signal electrode lines in the slice direction, the integrated circuit device further having a first surface and a second surface such that the terminals are positioned between the first surface and the second surface, the first surface facing in the one direction, the second surface facing in the other direction that is along the slice direction and opposite the one direction, both of the first surface and the second surface being positioned in the one direction relative to the all of the ultrasonic elements and positioned, relative to the signal terminal of each of the signal electrode lines, in the other direction, and each of the terminals of the integrated circuit device being connected to a corresponding one of the signal electrode lines.

2. The ultrasonic measurement device according to claim 1, wherein the ultrasonic element array is a rectangle, and when a long side direction of the rectangle is defined as a scan direction, and the integrated circuit device is mounted on the surface of the substrate such that a long side direction of the integrated circuit device extends along the scan direction.

3. The ultrasonic measurement device according to claim 1, wherein each of the ultrasonic elements has a first electrode, a second electrode, and a transducer section provided between the first electrode and the second electrode, and the first electrode or the second electrode extends on the substrate as the at least one signal electrode.

4. The ultrasonic measurement device according to claim 1, wherein the terminals in the integrated circuit device is configured by a projection electrode, and the integrated circuit device is subjected to flip chip mounting to the substrate.

5. The ultrasonic measurement device according to claim 1, further comprising a circuit element of the integrated circuit device formed on a silicon substrate, wherein the substrate of the ultrasonic transducer device is configured by silicon.

6. The ultrasonic measurement device according to claim 1, further comprising a vibration film of the ultrasonic element array formed on the substrate, wherein at least one of the signal electrodes extends on the vibration film.

7. The ultrasonic measurement device according to claim 6, further comprising a second integrated circuit device mounted on the substrate, wherein the ultrasonic element array is a rectangle, and the integrated circuit device is mounted in a first long side of the rectangle, and the second integrated circuit device is mounted in a second long side of the rectangle.

8. The ultrasonic measurement device according to claim 1, wherein the ultrasonic element array is a rectangle, and the integrated circuit device has a transmission circuit, which outputs the transmission signal, in each of the terminals, wherein when a long side direction of the rectangle is defined as a scan direction, in a state that the integrated circuit device is mounted on the surface of the substrate, the transmission circuits are arranged along the scan direction.

9. The ultrasonic measurement device according to claim 8, wherein the integrated circuit device has a transmission and reception selector switch, which is connected to the terminal, in each of the terminals, and the transmission and reception selector switches are arranged along the scan direction in the state that the integrated circuit device is mounted on the substrate.

10. The ultrasonic measurement device according to claim 8, wherein the integrated circuit device has a multiplexer arranged between the terminals, which is arranged along the scan direction, and the transmission circuits, which is arranged along the scan direction.

11. The ultrasonic measurement device according to claim 1, further comprising a protective film layer, which protects the ultrasonic element array, formed on the substrate and the integrated circuit device that is mounted on the substrate.

12. The ultrasonic measurement device according to claim 11, wherein the protective film layer is combined with an acoustic matching layer.

13. The ultrasonic measurement device according to claim 1, wherein the substrate has a plurality of openings arranged in an array pattern, each of the ultrasonic elements has a vibration film, which covers a corresponding one of the openings, and a piezoelectric element section provided on the vibration film, and the piezoelectric element section has a lower electrode provided on the vibration film, a piezoelectric film provided to cover at least a part of the lower electrode, and an upper electrode provided to cover at least a part of the piezoelectric film.

14. A head unit of a probe comprising:

the ultrasonic measurement device according to claim 1, wherein the head unit is removable with respect to a probe main body of the probe.

15. A probe comprising:
a probe main body;
a head unit having the ultrasonic measurement device according to claim 1, the head unit being removable with respect to the probe main body.

16. A diagnostic device comprising:
the ultrasonic measurement device described in claim 1, and
a display section which displays image data for display.

17. The ultrasonic measurement device according to claim 1, further comprising a flexible substrate electrically connected the signal terminal of each of the signal electrode lines and receiving a receiving signal from the ultrasonic element array.

18. The ultrasonic measurement device according to claim 1, further comprising a plurality of first control signal wires that extend in the one direction and a plurality of second control signal wires that extend in the one direction, wherein
the integrated circuit device further has a plurality of first control terminals and a plurality of second control terminals, the first control terminals are disposed at a side of a third surface of the integrated circuit device, the second control-terminals are disposed at a side of a fourth surface of the integrated circuit device, and the third surface and the fourth surface are opposite to each other in a scan direction perpendicular to the one and other directions.

19. The ultrasonic measurement device according to claim 18, wherein
the first control signal wires are connected to the first control terminals, respectively, and the second control terminals are connected to the second control terminals, respectively.

* * * * *